United States Patent
Kim et al.

(10) Patent No.: US 9,439,858 B2
(45) Date of Patent: Sep. 13, 2016

(54) TEMPERATURE SENSITIVE LIPOSOME INCLUDING CATIONIC LIPID AND USE THEREOF

(71) Applicant: Samsung Electronics Co., Ltd., Suwon-si, Gyeonggi-do (KR)

(72) Inventors: Hyun-Ryoung Kim, Guri-si (KR); Sang Joon Park, Yongin-si (KR); Min Sang Kim, Anseong-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 134 days.

(21) Appl. No.: 14/242,602

(22) Filed: Apr. 1, 2014

(65) Prior Publication Data

US 2014/0294932 A1   Oct. 2, 2014

(30) Foreign Application Priority Data

Apr. 1, 2013   (KR) .......................... 10-2013-0035290

(51) Int. Cl.
| | | |
|---|---|---|
| *A61K 9/127* | (2006.01) | |
| *A61K 31/713* | (2006.01) | |
| *A61K 31/519* | (2006.01) | |
| *A61K 31/365* | (2006.01) | |

(52) U.S. Cl.
CPC ............. *A61K 9/127* (2013.01); *A61K 9/1271* (2013.01); *A61K 9/1272* (2013.01); *A61K 31/365* (2013.01); *A61K 31/519* (2013.01); *A61K 31/713* (2013.01)

(58) Field of Classification Search
CPC ..................................................... A61K 9/127
See application file for complete search history.

(56) References Cited

U.S. PATENT DOCUMENTS

| | | |
|---|---|---|
| 7,745,651 B2 | 6/2010 | Heyes et al. |
| 2009/0232731 A1 | 9/2009 | Funk et al. |
| 2010/0203112 A1 | 8/2010 | Oh et al. |
| 2011/0200665 A1 | 8/2011 | Mei et al. |
| 2011/0268772 A1 | 11/2011 | Kim et al. |

FOREIGN PATENT DOCUMENTS

| | | |
|---|---|---|
| JP | 2003-212755 A | 7/2003 |
| KR | 2008-0000007 A | 1/2008 |
| KR | 2010-0076905 A | 7/2010 |
| KR | 2010-0087030 A | 8/2010 |
| KR | 2011-0077818 A | 7/2011 |

OTHER PUBLICATIONS

Dicheva et al. (Nano Letters. 2013 [published online May 22, 2012] 13: 2324-2331).*
Na et al. (Colloids and Surfaces B: Biointerfaces 91 (2012) 130-136; available online Nov. 2, 2011).*
Al-Ahmady et al. (ACSNANO (2012) 6(10): 9335-9346; available online Aug. 2, 2012).*
Oh et al., "Polymeric nanovehicles for anticancer drugs with triggering release mechanisms", *Journal of Materials Chemistry*, 17: 3987-4001 (2007).
Betre et al., A thermally responsive biopolymer for intra-articular drug delivery, *Journal of Controlled Release*, 115: 175-182 (2006).
Bikram et al., Thermo-responsive systems for controlled drug delivery, *Expert Opin. Drug Deliv.*, 5:1077-1091 (2008).
Dicheva et al., Cationic Thermosensitive Liposomes: A Novel Dual Targeted Heat-Triggered Drug Delivery Approach for Endothelial and Tumor Cells, *Nano Letters*,(13):2324-2331 (2013).

* cited by examiner

*Primary Examiner* — Scott Long
(74) *Attorney, Agent, or Firm* — Leydig, Voit & Mayer, Ltd.

(57) ABSTRACT

Provided are a liposome including a cationic lipid, a pharmaceutical composition for the delivery of anionic drugs, and a method for delivering anionic drugs to a target site.

20 Claims, 16 Drawing Sheets

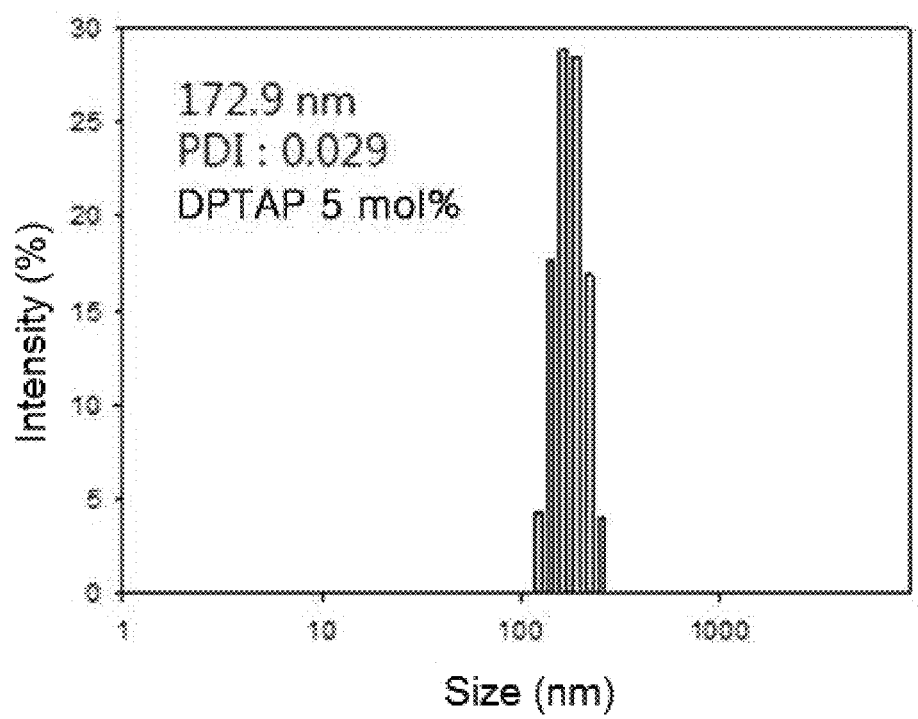

SEQUENCE LISTING

<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: Synthetic (unit of elastin-like polypetide,
      wherein Xaa is an amino acid except proline)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 1

Val Pro Gly Xaa Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic (unit of elastin-like polypetide,
      wherein Xaa is an amino acid except proline)
<220> FEATURE:
<221> NAME/KEY: misc_feature
<222> LOCATION: (3)..(3)
<223> OTHER INFORMATION: Xaa can be any naturally occurring amino acid

<400> SEQUENCE: 2

Pro Gly Xaa Gly Val
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic (unit of elastin-like polypetide,
      wherein Xaa is an amino acid except proline)
<220> FEATURE:
<221> NAME/KEY: misc_feature
<222> LOCATION: (2)..(2)
<223> OTHER INFORMATION: Xaa can be any naturally occurring amino acid

<400> SEQUENCE: 3

Gly Xaa Gly Val Pro
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic (unit of elastin-like polypetide,
      wherein Xaa is an amino acid except proline)
<220> FEATURE:
<221> NAME/KEY: misc_feature
<222> LOCATION: (1)..(1)
<223> OTHER INFORMATION: Xaa can be any naturally occurring amino acid

<400> SEQUENCE: 4

Xaa Gly Val Pro Gly
1               5

<210> SEQ ID NO 5
<211> LENGTH: 5
<212> TYPE: PRT
<213> ORGANISM: Artificial Sequence

```
<220> FEATURE:
<223> OTHER INFORMATION: Synthetic (unit of elastin-like polypetide,
      wherein Xaa is an amino acid except proline)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 5

Gly Val Pro Gly Xaa
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic (unit of Leucin zipper, wherein
      Xaa at 1st position is Val or Lys and Xaa
      at 3rd position is Ser or Lys)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 6

Xaa Ser Xaa Leu Glu Ser Lys
1               5

<210> SEQ ID NO 7
<211> LENGTH: 35
<212> TYPE: PRT
<213> ORGANISM: Artificial Sequence
<220> FEATURE:
<223> OTHER INFORMATION: Synthetic (Leucin zipper)

<400> SEQUENCE: 7

Val Ser Ser Leu Glu Ser Lys Val Ser Lys Leu Glu Ser Lys Lys Ser
1               5                   10                  15

Lys Leu Glu Ser Lys Val Ser Lys Leu Glu Ser Lys Val Ser Ser Leu
            20                  25                  30

Glu Ser Lys
        35

<210> SEQ ID NO 8
<211> LENGTH: 7
<212> TYPE: PRT
<213> ORGANISM: Artificial Sequence
<220> FEATURE:
<223> OTHER INFORMATION: Synthetic (amino acid sequence included in a
      peptide for targeting)

<400> SEQUENCE: 8

Cys Arg Gly Arg Arg Ser Thr
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic (amino acid sequence included in a
      peptide for targeting)

<400> SEQUENCE: 9
```

```
Cys Arg Ser Arg Lys Gly
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic (amino acid sequence included in a
      peptide for targeting)

<400> SEQUENCE: 10

Cys Lys Ala Ala Lys Asn Lys
1               5

<210> SEQ ID NO 11
<211> LENGTH: 19
<212> TYPE: RNA
<213> ORGANISM: Artificial Sequence
<220> FEATURE:
<223> OTHER INFORMATION: Synthetic (sense strand of GFP siRNA)

<400> SEQUENCE: 11
aacuucaggg ucagcuugc                                               19

<210> SEQ ID NO 12
<211> LENGTH: 19
<212> TYPE: RNA
<213> ORGANISM: Artificial Sequence
<220> FEATURE:
<223> OTHER INFORMATION: Synthetic (antisense strand of GFP siRNA)

<400> SEQUENCE: 12
gcaagcugac ccugaaguu                                               19

<210> SEQ ID NO 13
<211> LENGTH: 19
<212> TYPE: RNA
<213> ORGANISM: Artificial Sequence
<220> FEATURE:
<223> OTHER INFORMATION: Synthetic (sense strand of VEGR siRNA)

<400> SEQUENCE: 13
ggaguacccu gaugagauc                                               19

<210> SEQ ID NO 14
<211> LENGTH: 19
<212> TYPE: RNA
<213> ORGANISM: Artificial Sequence
<220> FEATURE:
<223> OTHER INFORMATION: Synthetic (antisense strand of VEGR siRNA)

<400> SEQUENCE: 14
gaucucauca ggguacucc                                               19
```

TEMPERATURE SENSITIVE LIPOSOME INCLUDING CATIONIC LIPID AND USE THEREOF

CROSS-REFERENCE TO RELATED APPLICATIONS

This application claims the benefit of Korean Patent Application No. 10-2013-0035290 filed on Apr. 1, 2013 in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 4,444 bytes ASCII (Text) file named "715829_ST25.TXT," created Apr. 1, 2014.

BACKGROUND

1. Field

A liposome containing cationic lipids, a pharmaceutical composition for the delivery of an anionic drug, and a method for delivering an active agent to a target are provided.

2. Description of the Related Art

A variety of biomaterials including liposomes, polymers, peptides, etc. have been used in drug delivery systems.

Liposomes have at least one lipid bilayer membrane enclosing an aqueous internal compartment. Liposomes may be characterized by membrane type and by size. Given a diameter of 20 nm to 50 nm, liposomes with a single membrane are classified as small unilamellar vesicles (SUV), while large unilamellar vesicles (LUV) have a diameter of greater than 50 nm. Large oligolamellar vesicles and large multilamellar vesicles may have multiple and optionally concentric membrane layers and be larger than 100 nm. Liposomes with several nonconcentric membranes, i.e., several smaller vesicles contained within a larger vesicle, are termed multivesicular vesicles.

A liposome is formulated to carry drugs or other active agents either contained within the aqueous inner space (water-soluble active agents) or partitioned into the lipid bilayer (water-insoluble active agents).

Active agents that have short half-lives in the bloodstream are particularly suited to delivery via liposomes. For example, many anti-neoplastic agents are known to have a short half-life in the bloodstream, and thus their parenteral use is not feasible. However, the use of liposomes for site-specific delivery of active agents via the bloodstream is severely limited by the rapid clearance of liposomes from the blood by cells of the reticuloendothelial system (RES).

A liposome may release part or all of its contents (e.g., "leak") if a hole is formed in the liposome membrane, if the membrane degrades or dissolves, or if the temperature of the membrane increases to a phase transition temperature. The elevation of temperature at a target site in a subject (hyperthermia) may increase the temperature of the liposome to a phase transition temperature or higher, thereby releasing liposome contents. This process may be applied to selectively deliver therapeutic agents. However, this technique is limited where the phase transition temperature of the liposome is significantly higher than the normal tissue temperature.

After extravasation, liposomes are more apt to be accumulated in tumors thanks to the EPR (enhanced permeation and retention) effect. In this case, the solid cancer-specific targeting efficiency is poor. To overcome this problem, the introduction of a targeting moiety into a liposomal surface has been suggested. Although increasing in tumor accumulation, immunoliposomes, which are designed to have antibodies or antibody fragments conjugated into liposomal surfaces, suffer from the problems associated with antibody construction, namely high production cost and difficult quality control due to poor reproducibility.

Separately, nanocarriers which extravasate drugs in response to internal stimuli have been studied. For example, nanocarriers have been designed to release drugs at low pH or in the presence of specific enzymes on the basis of the features of solid cancer such as low pH around the tumor, or overexpress specific enzymes. However, because these features of solid cancer vary depending on various factors including individual patients, the type and stage of cancer, etc., the nanocarriers taking advantage of these features are limited in universal applications to the treatment of cancer.

There is therefore a need for a carrier that is capable of efficiently delivering active agents.

SUMMARY

Provided herein is a liposome comprising a lipid bilayer, a thermosensitive peptide conjugated to a moiety comprising a hydrophobic group, and a cationic lipid, wherein the moiety comprising a hydrophobic group is positioned within the lipid bilayer. Also provided is a pharmaceutical composition for the delivery of an anionic drug including the liposome and the anionic drug, as well as a method for delivering an anionic drug to a target site using the liposome. These and other embodiments of the invention will be apparent from the following disclosures.

BRIEF DESCRIPTION OF THE DRAWINGS

FIGS. 3A, 3B, 3C, and 3D are graphs showing the size distributions of the liposomes (DPPC/DPTAP/DSPE-PEG/cholesterol/SA-V3-NH$_2$, anionic model drug: calcein) according to the content of DPTAP in phospholipid+DPTAP (FIG. 3A: 0 mol % DPTAP; FIG. 3B: 5 mol % DPTAP; FIG. 3C: 10 mol % DPTAP; FIG. 3D: 15 mol % DPTAP).

FIG. 4B: 10 mol % SA-(R)$_3$, FIG. 4C: 7.5 mol % SA-[(R)$_4$]; FIG. 4D: 10 mol % SA-[(R)$_4$].

DETAILED DESCRIPTION

Compared to other drugs, anionic drugs generally have short half-life in the bloodstream because of renal clearance, as well as very poor cellular uptake efficiency.

Anionic drugs, if entrapped within cationic liposomes, can have a prolonged half-life in serum and increased cellular uptake, when administered in a living body. In addition, when designed to be thermosensitive liposomes to extravasate drugs in response to external thermal stimuli, the cationic liposomes release the entrapped anionic drugs only when specific external thermal stimuli are present. Therefore, the cationic liposomes can be an alternative to the conventional liposome formulations which suffer from the disadvantage of having poor targeting efficiency for solid cancer upon systemic administration.

As used herein, the term "hydrophobic or hydrophobicity" refers to a physical property to be repelled from a mass of water. Hydrophobic molecules tend to be non-polar and, thus, prefer other neutral molecules and non-polar solvents. Hydrophobic molecules in water often cluster together, forming micelles. The term "hydrophilic or hydrophilicity" refers to a physical property to be attracted to, and tends to be dissolved by, water.

One embodiment provides a liposome including a cationic lipid. More particularly, the liposome may include a lipid bilayer, a thermosensitive peptide (for example, elastin-like polypeptide (ELP)) conjugated to a moiety including a hydrophobic group, and a cationic lipid. The hydrophobic group may be at least one selected from the group consisting of alkyl groups having 10 to 30 carbon atoms, 12 to 24 carbon atoms, 14 to 20 carbon atoms, or 16 to 20 carbon atoms (e.g., palmitoyl group, stearoyl group, arachidoyl group, etc.), but not be limited thereto.

In a particular embodiment, the liposome may further include a lipid bilayer stabilizing agent.

Figure 12:
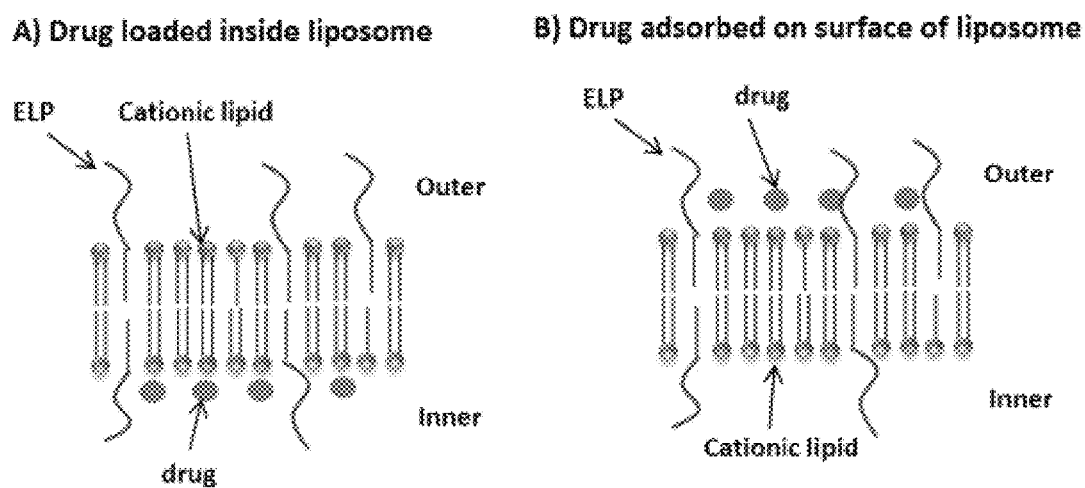
FIG. 12 is a schematic of liposomes with drugs entrapped therein or with drugs adsorbed to the surface thereof.

In another particular embodiment, the moiety including a hydrophobic group may be positioned in the lipid bilayer, and the thermosensitive peptide (such as elastin-like polypeptide) may be exposed to an inner space or an outer environment of the liposome (FIG. 12).

The term "lipid bilayer," as used herein, refers to a membrane composed of two layers of lipid molecules. The lipid layer may have a similar thickness to that of a naturally existing bilayer, for example, a cell membrane, a nuclear membrane, or a virus envelope. For example, the thickness of the lipid bilayer may be about 10 nm or less, e.g., about 1 nm to about 9 nm, about 2 nm to about 8 nm, about 2 nm to about 6 nm, about 2 nm to about 4 nm, or about 2.5 nm to about 3.5 nm.

Conventionally, a lipid bilayer serves as a barrier that keeps ions, proteins, and other molecules where they are needed and prevents them from diffusing into areas where they should not be. A lipid bilayer may include phospholipids. For example, natural lipid bilayers are made mostly of phospholipids. A phospholipid has a hydrophilic head and two hydrophobic tails. When phospholipids are exposed to an aqueous environment, they arrange themselves into a two-layered sheet (a bilayer) with the heads in contact with the surrounding environment, sequestering the hydrophobic tails in the center of the sheet. The center of this bilayer contains almost no water and also excludes molecules such as sugars or salts, which dissolve in water but not in oil. Phospholipids with certain head groups can alter the surface chemistry of a bilayer. Also, lipid tails may affect membrane properties, for instance, by determining the phase of the bilayer.

Lipid bilayers can adopt a solid gel phase state at lower temperatures but undergo phase transition to a fluid state at higher temperatures. In addition, the packing of different lipids within the bilayer affects its mechanical properties, including its resistance to stretching and bending. The different lipids available for the lipid bilayer may be found in animal cells. Representative among them is cholesterol, which helps strengthen the bilayer and decrease its permeability.

So long as it has a hydrophilic head and a hydrophobic tail, any "lipid molecule" may be used as a constituent of the lipid bilayer. It may have 12 to 50 carbon atoms and may be selected from the group consisting of phospholipids, sphingolipids, and glycolipids.

For instance, the lipid molecule may be a phospholipid that has a 12 to 22, e.g., 14 to 20 carbon atoms. The phospholipid may have two acyl groups, and may be selected from the group consisting of phosphatidyl cholines, phosphatidyl glycerols, phosphatidyl inositols, phosphatidyl ethanolamines, and combinations thereof. Also, the phospholipid may range in phase transition temperature from about 10° C. to about 70° C., e.g., from about 20° C. to about 65° C., from about 24° C. to about 55° C., from about 35° C. to about 45° C., from about 38° C. to about 45° C., from about 38° C. to about 42° C., from about 39° C. to about 45° C., or from about 39° C. to about 42° C. The acyl groups of the phospholipid may be saturated or unsaturated. The phospholipid may be a mixture of two or more different phospholipid molecules. Lipid bilayers having various phase transition temperatures may be produced from a mixture of two or more different phospholipid molecules.

A phospholipid molecule may have two acyl groups, and may be selected from the group consisting of a C12 saturated chain phospholipid (Tc=ca. 10° C.), a C1 saturated chain phospholipid (Tc=ca. 24° C.), a C16 saturated chain phospholipid (Tc=ca. 41° C.), a C18 saturated chain phospholipid (Tc=ca. 55° C.), a C20 saturated chain phospholipid (Tc=ca. 65° C.), a C22 saturated chain phospholipid (Tc=ca. 70° C.), and combinations thereof. Examples of the phospholipids include phosphatidylcholines, phosphatidyl glycerols, phosphatidyl inositols, and phosphatidyl ethanolamines.

Like phospholipids, sphingolipids such as sphingomyelins and glycolipids such as gangliosides, which vary in phase transition temperature depending on the chain length thereof, can be used as the lipid molecules.

Representative saturated chain phospholipids include dipalmitoylphosphatidylcholine (DPPC) for C16, 1,2-distearoyl-sn-glycero-3-phosphocholine (DSPC) for C18, and 1,2-dimyristoyl-sn-glycero-3-phosphocholine (DMPC) for C14, which have a bilayer transition temperature of about 41.5° C., about 55.10° C., and 23° C., respectively.

In one embodiment, the lipid molecule may be DPPC. In another embodiment, the phospholipid may be a mixture of two or more different phospholipid molecules at such a ratio that the phase transition temperature is adjusted to a desired one.

In addition to phospholipids, other membrane-forming lipids may be employed in the lipid bilayer. Examples of the lipids other than phospholipids, which are available for the formation of the lipid bilayer structure, include bola lipids and bacterial lipids. Moreover, the lipid bilayer may contain a block copolymer including a water-soluble polymer (e.g., polyethylene glycol) and a water-insoluble polymer (e.g., polypropylene oxide and polyethylethylene).

The term "primary lipid," as used in the context of a liposome bilayer, refers to a main lipid component of liposome bilayer materials. For example, when a liposome bilayer is composed of 70 mol % phospholipid and 30 mole % cholesterol, the primary lipid of the liposome bilayer is phospholipid. In a liposome bilayer according to one embodiment, the primary lipid (e.g., phospholipid) may be present in an amount of about 51 to 100 mol %, for example, about 85 to 100 mol %, based on the total mole amount of the lipid bilayer.

A lipid bilayer may have different phase behaviors that change with temperature. At a given temperature a lipid bilayer can exist in either a liquid or a gel (solid) phase. All lipids have a characteristic temperature at which they transition from the gel to liquid phase. In both phases the lipid molecules are prevented from flip-flopping across the bilayer, but in liquid phase bilayers, a given lipid will exchange locations with its neighbor. This random walk exchange allows lipids to diffuse and thus wander across the surface of the membrane. Unlike liquid phase bilayers, the lipids in a gel phase bilayer are locked in place.

The phase behavior of lipid bilayers is largely determined by the strength of the attractive Van der Waals interactions between adjacent lipid molecules. Longer tailed lipids have more area over which to interact, increasing the strength of this interaction and consequently decreasing the lipid mobility. Thus, at a given temperature, a short-tailed lipid will be more fluid than an otherwise identical long-tailed lipid.

Transition temperature can also be affected by the degree of unsaturation of the lipid tails. An unsaturated double bond can produce a kink in the alkane chain, disrupting the lipid packing. This disruption creates extra free space within the bilayer which allows additional flexibility in the adjacent chains.

Most natural membranes are a complex mixture of different lipid molecules. If some of the components are liquid at a given temperature while others are in the gel phase, the two phases can coexist in spatially separated regions, rather like an iceberg floating in the ocean.

As used herein, the term "phase transition temperature" refers to a temperature at which a material changes from a solid phase to a liquid phase (also called a melting temperature) or from a liquid phase to a solid phase. The material may be a lipid molecule, a lipid bilayer or liposome having a thermosensitive peptide (e.g., an elastin-like polypeptide) conjugated to a moiety including a hydrophobic group, or a lipid bilayer or liposome having a thermosensitive peptide (e.g., elastin-like polypeptide) conjugated to a moiety including a hydrophobic group.

Liposomes may not accumulate in leaky tumor tissue because they exhibit a relatively short half-life in circulating blood due to their rapid uptake by macrophages of the liver and spleen (organs of the endothelial system or reticuloendothelial system (RES)). A liposome preparation according to one embodiment of the present invention may be devised to avoid rapid RES uptake and thus increase circulation times. In this regard, the lipid bilayer may contain, for example, lipids derivatives derivatized with hydrophilic polymers, for example phospholipids derivatives. The hydrophilic polymers may be selected from the group consisting of polyethylene glycol, polylactic acid, polyglycolic acid, copolymers of polylactic acid and polyglycolic acid, polyvinyl alcohols, polyvinyl pyrrolidone, oligosaccharides, and mixtures thereof. The hydrophilic polymer may range in average molecular weight from 100 to 100,000 Da. The lipid derivatives derivatized with the hydrophilic polymers may be phospholipids of C4-C30, for example C16-C24, conjugated with PEG. The derivatives may be DPPC-PEG or DSPE (1,2-distearoyl-sn-glycero-3-phosphoethanolamine)-PEG. The PEG may have a weight average molecular weight of about 180 to about 50,000 Da.

Having a lipid bilayer structure which exhibits phase transition depending on temperature, the liposome according to the present invention can release the content entrapped therein as the lipid molecules which reach their melt points transition into a liquid phase to disrupt the lipid bilayer structure when the temperature is suitably control. That is, given a specific temperature, the lipid bilayer structure of the liposomes is destroyed to extravasate an active agent entrapped inside the liposomes into a desired region where the liposomes reach after administration. Thus, the liposomes according to the present invention allow the entrapped active agent to release into a desired region even after systemic administration.

The liposome may include a thermosensitive peptide conjugated with a moiety including a hydrophobic group, wherein the moiety including a hydrophobic group is positioned in the lipid bilayer. So long as it undergoes a conformational change with an increase or decrease in temperature as a consequence of the formation or destruction of intra- and/or intermolecular hydrogen bonds, any thermosensitive peptide may be employed in the present invention. For example, the conformational change which is induced by temperature elevation may be based on a change of the secondary structure of the thermosensitive peptide from a random coil to α-helix or β-turn, contributing to the phase transition of the liposome. The thermosensitive peptide available for the construction of the liposome may be selected from the group consisting of elastin-like polypeptide (ELP), a leucine zipper motif, a silk-like peptide, and a combination thereof, and is preferably an elastin-like polypeptide (ELP) or a leucine zipper motif.

The moiety including a hydrophobic group may be positioned between lipid molecules of the lipid bilayer, that is, within the interior of the lipid bilayer (regions where the hydrophobic tails of each layer of the lipid bilayer are located), participating in the construction of the lipid bilayer, and functioning to immobilize the thermosensitive peptide conjugated thereto to the lipid bilayer. The moiety including a hydrophobic group may be a lipid molecule which is the same as or different from a lipid molecule forming the lipid portion of a bilayer, The moiety including a hydrophobic group may be selected from the group consisting of a hydrophobic molecule, an amphipathic molecule containing both hydrophobic and hydrophilic portions, and a combination thereof. As for the amphipathic molecule, its hydrophobic portion is disposed inward of the lipid bilayer while the hydrophilic portion is arranged outward of the lipid bilayer. In this regard, the thermosensitive peptide may be conjugated to the hydrophilic portion, being exposed to the exterior of the lipid bilayer (that is, exterior or interior of the liposome). Where the hydrophobic molecule is conjugated to a thermosensitive peptide, the hydrophobic molecule is disposed inward of the lipid bilayer while the thermosensitive peptide is arranged outward of the lipid bilayer, being exposed to the exterior of the lipid bilayer (that is, exterior or interior of the liposome). Here, "outward" of the lipid bilayer indicates a direction away from a center of the lipid bilayer (a region where the hydrophobic tails of each layer of the lipid bilayer are located), that is, inward or outward of the liposome.

The moiety including a hydrophobic group may be a lipid molecule found in natural biomembranes, or may be selected from among lipid molecules which can be involved in the construction of a lipid bilayer although not naturally existing in biomembranes.

Among the lipid molecules naturally existing in biomembranes may be phospholipids or their derivatives, sterols or their derivatives, and sphingolipids or their derivatives. The phospholipids or their derivatives may be selected from the group consisting of phosphatidyl cholines, phosphatidyl glycerols, phosphatidyl inositols, phosphatidyl ethanolamines, and combinations thereof. The sterols or their derivatives may be cholesterols or their derivatives, or squalenes or their derivatives. The sphingolipids may be sphingomyelins or their derivatives, or gangliosides or their derivatives. The phospholipids, sterols, or sphingolipids include intermediates or precursors produced during a synthesis process in vivo. For example, the moiety including a hydrophobic group includes phosphoglycerides, sphingosines, ceramides, cerebrosides, or any combination thereof.

The moiety including a hydrophobic group may be a saturated or unsaturated hydrocarbon, a saturated or unsaturated acyl molecule, or a saturated or unsaturated alkoxy molecule, with C4-C30, for example, C14-C24 or C16-C24.

A conjugation of a moiety including a hydrophobic group and a thermosensitive peptide may be mediated via a cleavable linkage that may be cleaved under physiological or pathological conditions. An example of the cleavable linkage may be a linkage mediated by a pH cleavable linker, a heat cleavable linker, a radiation cleavable linker, or a linker that is cleaved in an aqueous solution.

The moiety including a hydrophobic group may be conjugated to a side chain or a terminus of the thermosensitive peptide via the hydrophobic group (e.g., C16-20 alkyl group). For example, the moiety including a hydrophobic group (e.g., the hydrophobic group included in the moiety) may be linked to a nitrogen atom at the N-terminus or a carbonyl (—C(O)—) group at the C-terminus of the thermosensitive peptide. Alternatively, the moiety including a hydrophobic group (e.g., the hydrophobic group included in the moiety) may be conjugated to the thermosensitive peptide by interaction with a functional group of the thermosensitive peptide, for example a functional group selected from among an amino group, a carbonyl group, a hydroxyl group, a thiol group, and a combination thereof. In another alternative, the moiety including a hydrophobic group (e.g., the hydrophobic group included in the moiety) may be conjugated to the thermosensitive peptide through an amine bond or amide bond with a nitrogen atom of the thermosensitive peptide, or through an amide or ester bond with the carbonyl group of the thermosensitive peptide. The moiety including a hydrophobic group may be a moiety containing a hydrophobic group with a single chain.

As the moiety including a hydrophobic group, an aliphatic hydrocarbon containing 4 to 30 carbon atoms, for example, 14 to 24 carbon atoms or 16 to 24 carbon atoms, may be used. The moiety including a hydrophobic group may be, for example, myristoyl (C14), palmitoyl (C16), stearoyl (C18), arachidonyl (C20), behenoyl (C22), or lignoceryl (C24). The moiety including a hydrophobic group is positioned in a lipid bilayer by a hydrophobic effect, so that the thermosensitive peptide conjugated to the moiety including a hydrophobic group may be immobilized on the liposome.

As used herein the term "thermosensitive peptide" refers to a class of amino acid polymers that undergo a conformational change dependent upon temperature. For example, it may be selected from the group consisting of an elastin-like polypeptide (ELP), a leucine zipper motif, a silk-like peptide, and a combination thereof.

In an embodiment, the thermosensitive peptide, such as the ELP, leucine zipper motif, and silk-like peptide, may be a polymer exhibiting inverse phase transitioning behavior. Inverse phase transitioning behavior indicates that the thermosensitive peptides are soluble in aqueous solutions at below an inverse transition temperature ($T_t$), while becoming insoluble as the temperature is raised higher than the $T_t$. By increasing the temperature, thermosensitive peptides transition from elongated chains that are highly soluble into tightly folded aggregates that are greatly reduced in solubility. Such inverse phase transition may be induced as thermosensitive peptide structures have more β-turn structures and distorted β-structures with an increase in temperature. In some cases, the thermosensitive peptides may be defined based on the phase transitioning temperature. By way of example, the phase transition may occur at a temperature of about 10° C. to about 70° C., for example, from about 35° C. to about 45° C., from about 38° C. to about 45° C., from about 39° C. to 45° C., from about 38° C. to about 42° C., or from about 39° C. to about 42° C.

When thermosensitive peptides are linked to the components of a lipid bilayer, the inverse phase transitioning behavior may destroy the β lipid bilayer due to the shrinkage and self-assembly of the thermosensitive peptides as the temperature rises from lower than to higher than $T_t$ of the thermosensitive peptides. Destroying the lipid bilayer may increase the permeability of the lipid bilayer. Thus, active agents entrapped inside a liposome including the lipid bilayer may be released with higher permeability from the liposome. However, the release of active agents from liposomes according to the present invention is not limited to any particular mechanism of action.

The destruction of the lipid bilayer in a liposome by the inverse phase transitioning behavior of thermosensitive peptides is dependent on lipid molecules of the lipid bilayer, that is, the phase transition temperature of the lipid bilayer. A lipid bilayer exists as a gel phase at the phase transition temperature or below and as a liquid (crystalline) phase at higher than the phase transition temperature. When the lipid bilayer exists in a gel phase, the structure of the lipid bilayer may not be destroyed or may be limitedly destroyed even though the thermosensitive peptide conformationally changes to a β-turn structure due to the inverse phase transitioning behavior. On the other hand, when the lipid bilayer is in a liquid phase, the destruction of the lipid bilayer may be induced as the thermosensitive peptide conformationally changes to a β-turn structure due to the inverse phase transitioning behavior. In other words, when the lipid bilayer exists in a liquid phase rather than in a gel phase, the inverse phase transition induces the lipid bilayer to collapse more efficiently. Therefore, a releasing temperature at which the active agents start to be extravasated from the liposome may be controlled by adjusting the phase transition temperature of a lipid bilayer of the liposome or the inverse phase transition temperature of the thermosensitive peptide. For example, the phase transition temperature of a lipid bilayer or a liposome including a thermosensitive peptide may range from about 10° C. to about 70° C., for example, from about 10° C. to about 60° C., from about 10° C. to about 55° C., from about 10° C. to about 45° C., from about 20° C. to about 60° C., from about 20° C. to about 55° C., from about 30° C. to about 55° C., from about 30° C. to about 45° C., from about 35° C. to about 45° C., from about 38 to about 45° C., from about 39° C. to about 45° C., from about 38° C. to about 42° C., or from about 39° C. to about 42° C.

A liposome including a thermosensitive peptide according to one embodiment of the present invention can release an active agent entrapped in the liposome more effectively than can a liposome free of thermosensitive peptides, such as a liposome composed of a lipid bilayer only. When only the phase transition of lipid molecules of a lipid bilayer is used, the release of active agents from the liposome is induced by dispersion of the lipid molecules. In contrast, a liposome including ELPs allows active agents to be released more effectively because the release is induced by the inverse phase transitioning behavior of the thermosensitive peptide, that is, the shrinkage and assembly of the thermosensitive peptide, as well as by the diffusion of the lipid molecules. In this context, the active agent may be contained in the inner space of the liposome or within the lipid bilayer.

In an embodiment, the ELP may be defined by its amino acid sequence. A part of or an entire ELP may include one or more repeating units which are selected from the group consisting of VPGXG (SEQ ID NO: 1), PGXGV (SEQ ID NO: 2), GXGVP (SEQ ID NO: 3), XGVPG (SEQ ID NO: 4), GVPGX (SEQ ID NO: 5), and a combination thereof, wherein V stands for valine, P for proline, G for glycine, and X for any natural or non-natural amino acid residue except proline (alanine, isoleucine, leucine, methionine, phenylalanine, tryptophan, valine, asparagine, cysteine, glutamine, glycine, serine, threonine, tyrosine, aspartic acid, glutamic acid, arginine, histidine, or lysine). Here, X in each repeating unit may be the same or different, and for example, may be valine or alanine independently.

The repeating units may be separated by one or more amino acids that can maintain the phase transition property of ELP, or may be different at the terminus by one or more amino acids or linkers. For instance, X on one or more repeating units of SEQ ID NOS: 1 to 5 may be an amino acid having an amine as a side chain, such as lysine or arginine. In this case, a lipid, or a linker incorporated into a liposome membrane like a lipid, may be bound to the terminal amine group which is a side chain of the substituted amino acid. Therefore, in one embodiment, X may be valine, alanine, or an amino acid having an amine group as a side chain, e.g., lysine or arginine.

A ratio of the repeating units versus the other amino acids or linker moieties having an amine group as a side chain may be about 0.1 to about 99.9% based on the total amino acids of both the repeating units and the other amino acids. The repeating unit(s) may be repeated twice or more, for example, about 2 to about 200 times or more.

In an embodiment, the elastin-like polypeptide may be in the form of blocks, where any one or more of VPGXG, PGXGV, GXGVP, XGVPG, GVPGX, or a combination thereof is tandemly repeated, or may include a block in which VPGXG, PGXGV, GXGVP, XGVPG, GVPGX, or a combination thereof is tandemly repeated one or more times. If retaining the inverse phase transitioning behavior, the elastin-like polypeptide may include not only VPGXG, PGXGV, GXGVP, XGVPG, GVPGX, or a combination thereof, but also other portions, for example, the above-mentioned linkers and/or blocks, within the molecule. The elastin-like polypeptide may be linked at the N- or C-terminus with a moiety including a hydrophobic group. Alternatively, or in addition, the conjugation between a moiety including a hydrophobic group and the elastin-like polypeptide may be achieved by linking the moiety including a hydrophobic group to a functional group or the terminus of the side chain of the polypeptide. The functional group of the side chain may be an amino group, a hydroxyl group, a thiol group, or a carboxyl group.

In the elastin-like polypeptide, the other terminus which is not linked with a moiety including a hydrophobic group may be blocked or unblocked. For example, when a moiety including a hydrophobic group and an elastin-like polypeptide are linked via the N-terminus of the elastin-like polypeptide, a carboxyl group of the C-terminus of the elastin-like polypeptide may be blocked or unblocked. The blocking may be achieved by linking or interacting with a material that may be biocompatible, non-immunogenic, helpful in a specific delivery, or avoidable with regard to the biological degradation system. For example, the blocking may be achieved by forming an amide bond between the terminal carboxyl group of the elastin-like polypeptide and an amino group. The amino group may come from an ammonia molecule, a primary amine, a secondary amine, or a tertiary amine. The primary, secondary, or tertiary amine may each have 1 to 10 carbon atoms, for example, 1 to 6 carbon atoms.

The repeating units may be independently repeated one or more times, for example, 1 to 200 times, 1 to 100 times, 1 to 80 times, 1 to 60 times, 1 to 40 times, 1 to 10 times, 1 to 12 times, 1 to 8 times, 1 to 6 times, 2 to 200 times, 2 to 100 times, 2 to 80 times, 2 to 60 times, 2 to 40 times, 2 to 10 times, 2 to 12 times, 2 to 8 times, 2 to 6 times, 4 to 100 times, 8 to 80 times, 10 to 60 times, 12 to 40 times, 20 to 40 times, 4 to 10 times, 4 to 8 times, or 4 to 6 times.

For example, the moiety including a hydrophobic group-conjugated elastin-like polypeptide may be palmitoyl-(VPGXG)n or stearoyl-(VPGXG)n (wherein n is an integer of 1 to 12, for example, 2 to 6).

Leucine zippers contain a repeated pattern composed of 7 amino acids, referred to as a heptad repeat. The positions in the heptad repeat are usually labeled abcdefg, where d, together with a, are the hydrophobic positions, usually being occupied by leucine. A leucine zipper retains an α-helix conformation at the phase transition temperature, while the amino acids at a and d are arranged on one side of the helical structure, forming a coiled-coil conformation. At higher than the phase transition temperature, the coiled-coil domain is dissociated to give a disordered peptide.

The leucine zipper may be linked at the N- or C-terminus with a moiety including a hydrophobic group. Alternatively, or in addition, the conjugation between a moiety including a hydrophobic group and the leucine zipper may be achieved by linking the moiety including a hydrophobic group to a functional group or the terminus of the side chain of the leucine zipper. The functional group of the side chain may be an amino group, a hydroxyl group, a thiol group, or a carboxyl group. In the leucine zipper, the terminus which is not linked with a moiety including a hydrophobic group may be blocked or unblocked. For example, when a moiety including a hydrophobic group and a leucine zipper are linked via the N-terminus of the leucine zipper, a carboxyl group of the C-terminus of the leucine zipper may be blocked or unblocked. The blocking may be achieved by linking or interacting with a material that may be biocompatible, non-immunogenic, helpful in a specific delivery, or avoidable with regard to the biological degradation system. For example, the blocking may be achieved by forming an amide bond between the terminal carboxyl group of the leucine zipper and an amino group. The amino group may come from an ammonia molecule, a primary amine, a secondary amine, or a tertiary amine. The primary, secondary, or tertiary amine may each have 1 to 10 carbon atoms, for example, 1 to 6 carbon atoms.

A leucine zipper may be represented by [XSZLESK]n in which the repeating unit [XSZLESK] (SEQ ID NO: 6) is repeated n times. In each repeating unit, X is independently valine (V) or lysine (K), Z is independently serine (S) or lysine (K), and n means the number of the repeating units, being an integer of at least one. The repeating units [XSYLESK], when repeated two or more times, are the same or different. For instance, the number of repeating units may be an integer of 1 to 200, 1 to 100, 1 to 80, 1 to 60, 1 to 40, 1 to 10, 1 to 12, 1 to 8, 1 to 6, 2 to 200, 2 to 100, 2 to 80, 2 to 60, 2 to 40, 2 to 12, 2 to 10, 2 to 8, 2 to 6, 4 to 100, 8 to 80, 10 to 60, 12 to 40, to 40, 4 to 10, 4 to 8, or 4 to 6. In one embodiment of the present invention, the leucine zipper has the sequence of [VSSLESK-VSKLESKKSKLESKVSKLESKVSSLESK]-NH2 (SEQ ID NO: 7-NH2).

In the liposome, a molar ratio of primary lipid molecules (e.g., phospholipids) of the lipid bilayer:thermosensitive peptide (e.g., an elastin-like polypeptide or leucine zipper) conjugated to a moiety including a hydrophobic group may be appropriately selected according to properties of the selected lipid bilayer and the thermosensitive peptide conjugated to a moiety including a hydrophobic group. For example, a molar ratio of primary lipid molecules:thermosensitive peptide conjugated to a moiety including a hydrophobic group may be about 50 to about 99.9:about 0.1 to about 50, or about 99.9:about 0.1 to about 90:about 10. For example, a molar ratio of primary lipid molecules (DPPC or mixtures of DPPC and DSPC):moiety including a hydrophobic group-conjugated elastin-like peptide (palmitoyl-(VPGXG)n or stearoyl-(VPGXG)n (where n is independently an integer of 2 to 12)) or a moiety including a hydrophobic group-conjugated leucine zipper (palmitoyl-[XSZLESK]n or stearoyl-[XSZLESK]n (where X is valine (V) or lysine (K), Y is serine (S), or lysine (K), and n is an integer of 2 to 12)) may be about 50 to about 99.0:about 0.1 to about 50, or about 99.9:about 0.1 to about 90:about 10.

Figure 5:
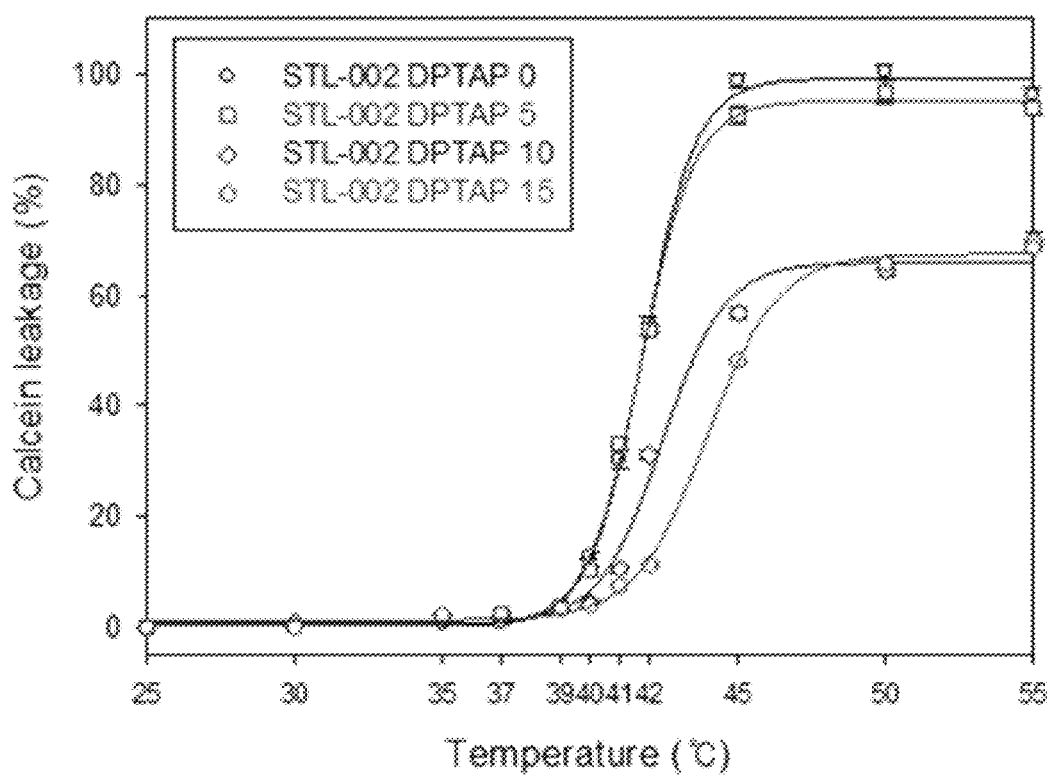
FIG. 5 is a graph showing the temperature release profiles of calcein from the liposomes (DPPC/DSPC/DPTAP/DSPE-PEG/cholesterol/SA-V3-NH$_2$, anionic model drug: calcein) according to DPTAP content.

The liposome includes a cationic lipid. When forming a complex with an anionic drug (particularly siRNA) via electrostatic interaction (attraction), the cationic lipid functions to entrap anionic drugs within the liposome. In addition, even after the lipid bilayer collapses at higher than the phase transition temperature, the cationic lipid holds the anionic drug by electrostatic attraction. That is, not only do the cationic lipids function to entrap anionic drugs within the liposomes, but also when the anionic drugs are released as the lipid bilayer is destroyed at a target site, the cationic lipids control the release rate of the drugs by restraining the rapid release in an early stage, and thus regulate the release amount (FIG. 5).

Any cationic lipid that forms a complex with an anionic drug by electrostatic interaction may be employed in the present invention. Examples of the cationic lipid include 1,2-dipalmitoyl-3-trimethylammonium-propane (DPTAP), 1,2-dioleoyl-3-trimethylammonium-propane (DOTAP), N,N-dioleyl-N,N-dimethylammonium chloride (DODAC), N,N-distearyl-N,N-dimethylammonium bromide (DDAB), N-(1-(2,3-dioleoyloxy)propyl-N,N,N-trimethylammonium chloride, N,N-dimethyl-(2,3-dioleoyloxy)propylamine (DODMA), N,N,N-trimethyl-(2,3-dioleoyloxy)propylamine (DOTMA), 1,2-diacyl-3-trimethyl ammonium-propane (TAP), 1,2-diacyl-3-dimethyl ammonium-propane (DAP), 3beta-[N—(N',N',N'-trimethylaminoethane)carbamoyl]cholesterol (TC-cholesterol), 3beta[N—(N',N'-dimethylaminoethane)carbamoyl]cholesterol (DC-cholesterol), 3beta[N—(N'-monomethylaminoethane)carbamoyl]cholesterol (MC-cholesterol), 3beta[N-(aminoethane)carbamoyl]cholesterol (AC-cholesterol), cholesteyloxypropane-1-amine (COPA), N—(N'-aminoethane)carbamoylpropanoic tocopherol (AC-tocopherol), and N—(N'-methylaminoethane)carbamoylpropanoic tocopherol (MC-tocopherol). In addition, the cationic lipid may be a lipid conjugate in which a fatty acid of C12 to C22, for example, C14 to C20 or C16 to C18, is conjugated with 1 to 10, for example 1 to 9, 3 to 9, or 3 to 5 repeats of a cationic amino acid selected from among arginine, histidine, lysine, and a combination thereof.

In one embodiment, the cationic lipid may be DPTAP or DOTAP, or a lipid conjugate in which a fatty acid of C16 to C18 (e.g., stearic acid) is conjugated with 1 to 9 repeats of a cationic amino acid (e.g., arginine).

The cationic lipid may form a complex with an anionic drug by electrostatic interaction. In this complex, the anionic drug is entrapped in such a manner that the cationic lipid is located between the lipid molecules of the lipid bilayer while the anionic drug is confined within the inner space of the liposome. As described above, the complex of the cationic lipid with an anionic drug prevents the initial burst of the drug, and controls the release rate of the drug when the bilayer degrades at a target site.

In order to form a complex between the cationic lipid and the anionic drug through an electrostatic interaction, a charge ratio between the anionic drug (N) and the cationic lipid (P) (N/P: charge ratio of negative charge to positive charge) is set forth within a range of 0.1 to 128, preferably within a range of 0.5 to 32, and more preferably within a range of 1 to 16, in accordance with one embodiment. For example, if the ratio (N/P) is below 0.1, it is difficult to form a complex in which a sufficient amount of the anionic drug is contained. At an N/P ratio greater than 0.1, a complex with a sufficient amount of anionic drugs entrapped thereinto can be obtained On the other hand, at an N/P ratio greater than 128, the complex is more apt to cause cytotoxicity. Thus, the N/P ratio is recommended to be set below 128.

The liposome may further include a lipid bilayer stabilizing agent. In a liposome including a thermosensitive peptide, such as an elastin-like polypeptide, a leucine zipper, etc., a lipid bilayer stabilizing agent may be introduced into the lipid bilayer to enhance the stability of the lipid bilayer, and also to effectively release the active agent. The stabilizing agent may be a lipid which is higher in phase transition temperature than is the lipid bilayer. In one embodiment, the lipid bilayer stabilizing agent may be selected from the group consisting of steroids, glycolipids, sphingolipids, and a combination thereof.

For example, the lipid bilayer stabilizing agent may be a steroid compound which can be incorporated into a lipid bilayer. As used herein, the term "steroid" refers to a type of organic compound with a chemical structure that contains gonane or a skeleton derived therefrom. The gonane is composed of seventeen carbon atoms bonded together that take the form of four fused rings: three cyclohexane rings (designated as rings A, B, and C from the left to the right) and one cyclopentane ring (the D ring). Herein, the term "skeleton derived therefrom" refers to a gonane derivative wherein an unsaturated bond is introduced into the gonane skeleton. The steroids may vary depending on the functional groups attached to the four ring core and the oxidation state of the rings. For example, the steroids may contain a hydrophilic functional group on the ring. In one embodiment, the steroids may have a hydroxyl group on the ring.

The steroids may be sterols. The term "sterol" refers to a type of steroid which has the hydroxyl group at position C-3 and has a skeleton derived from cholestane. Herein, the term "a skeleton derived from cholestane" refers to a skeleton wherein an unsaturated bond is introduced into the cholestane skeleton. The steroids naturally occur in plants, animals, and fungi. For example, all steroids may be made in cells either from lanosterol as in animals and fungi, or from cycloartenol as in plants. The sterols may be cholesterols or their derivatives. Herein, "derivative" means a derivate of cholesterol which maintains the property of being incorporated into a lipid bilayer. The cholesterol or its derivative may be at least one selected from the group consisting of cholesterols, sitosterols, ergosterols, stigmasterols, 4,22-stigmastadien-3-ones, stigmasterol acetates, lanosterols, and cycloartenols, or any combination thereof.

According to one embodiment, the stabilizing agents may be selected from the group consisting of cholesterols, sitosterols, ergosterols, stigmasterols, 4,22-stigmastadien-3-ones, stigmasterol acetates, lanosterols, cycloartenols, and combinations thereof.

The stabilizing agent is helpful for reinforcing the lipid bilayer and lowering the permeability of the liposome. For example, cholesterol serves to make the liposome stable at a normal body temperature.

If a stabilizing agent, e.g., cholesterol, is incorporated into a liposome comprising a lipid bilayer only, without a thermosensitive peptide (e.g., an elastin-like polypeptide or leucine zipper), the ability of the liposome to release an active agent is significantly reduced. Thus, the use of a lipid bilayer stabilizing agent allows the liposome containing a thermosensitive polypeptide to effectively release an active agent while maintaining the integrity of the lipid bilayer or the liposome. Particularly, the liposome can effectively release a drug within a narrow temperature range, for example, from about 39° C. to about 45° C.

To construct desired liposomes in an aqueous environment, components of the liposome must be appropriately controlled.

In one embodiment, a molar ratio of a total of primary lipids (e.g., phospholipids) and cationic lipids of the lipid bilayer:moiety including a hydrophobic group-conjugated thermosensitive peptide (e.g., elastin-like peptide or leucine zipper) may be on the order of 100:0.1 to 5, preferably on the order of 100:0.2 to 3, and more on the order of 100:0.5 to 2.

In one embodiment where the liposome contains a lipid derivative derivatized with a hydrophilic derivative in the lipid bilayer, the molar ratio of a total of primary lipids and cationic lipids of the lipid bilayer:lipid derivative derivatized with a hydrophilic polymer (e.g., DPPC-PEG, or DSPE-PEG) may be on the order of 100:0.5 to 20, preferably on the order of 100:1 to 10, and more preferably on the order of 100:2 to 5.

When the liposome further contains a lipid bilayer stabilizing agent, the molar ratio of a total of primary lipids and cationic lipids of the lipid bilayer:lipid bilayer stabilizing agent (e.g., cholesterol) may be on the order of 100:5 to 50, preferably on the order of 100:10 to 40, and more preferably on the order of 100:15 to 35.

Based on 100 moles of a total of primary lipids and cationic lipids of the lipid bilayer, the molar ratio of primary lipid:cationic lipid may be on the order of 85 to 99:1 to 15, and preferably on the order of 90 to 99:1 to 10.

In one embodiment, the liposome may further include a targeting moiety to enhance targeting efficiency and/or accumulation in a target site (e.g., tumor or inflammatory region).

The targeting moiety useful in the present invention may be selected from the group consisting of a peptide including an RGD sequence or its derivative, biotin or its derivative, folate or its derivative, an antibody specific to an antigen of a cancer cell or a tumor cell, an antibody fragment or its derivative specific to an antigen of a cancer cell or a tumor cell, a ligand or its derivative binding to a receptor characteristic of cancer cells or inflammatory regions, and a combination thereof. The RGD derivative may be an R*GDYK* peptide (wherein * represents the position of a cyclized amide linkage (—CO—NH—)). Alternatively, the derivative is a cyclic peptide having an RGD sequence, a cyclized amide bond (—CO—NH—), and an active hydrosulfide group at a terminal of a cysteine. In one embodiment, the cyclic peptide has an amino acid sequence represented by X*YRGDYZ*, wherein * indicates a position of the cyclization, X is a cysteine residue containing a free hydrosulfide group, Y represents one or more amino acids, or an amino acid sequence of an appropriate length, and Z represents an amino acid that can form a ring with a cysteine residue. In another embodiment, the cyclic peptide may have an amino acid sequence represented by X*GRGDSPZ*, wherein * indicates a position of the cyclization, X is a cysteine residue containing a free hydrosulfide group, and Z represents one or more amino acids, or an amino acid sequence of an appropriate length. In a further embodiment, the cyclic peptide may have an amino acid sequence represented by X*GRGSPK*, wherein * indicates a position of the cyclization and X is a cysteine residue containing a free hydrosulfide group. The targeting moiety, such as an RGD sequence or its derivative, may be linked to a lipid through an appropriate linker such as a succinyl group.

Examples of RGD containing cyclic peptides include a cyclo (Arg-Gly-Asp-D-Phe-Cys)*(c(RGDfC, M.W. 578.65), linker additions via Cys).

For example, the targeting moiety may be linked to a lipid molecule, existing in the form of DSPE-cRGDYK. Here, the targeting moiety may be cRGDYK-CO—(CH$_2$)$_3$—(CO)— in which an RGD derivative is bound to a linker (as shown in the following Chemical Formula 1).

[Chemical Formula 1]

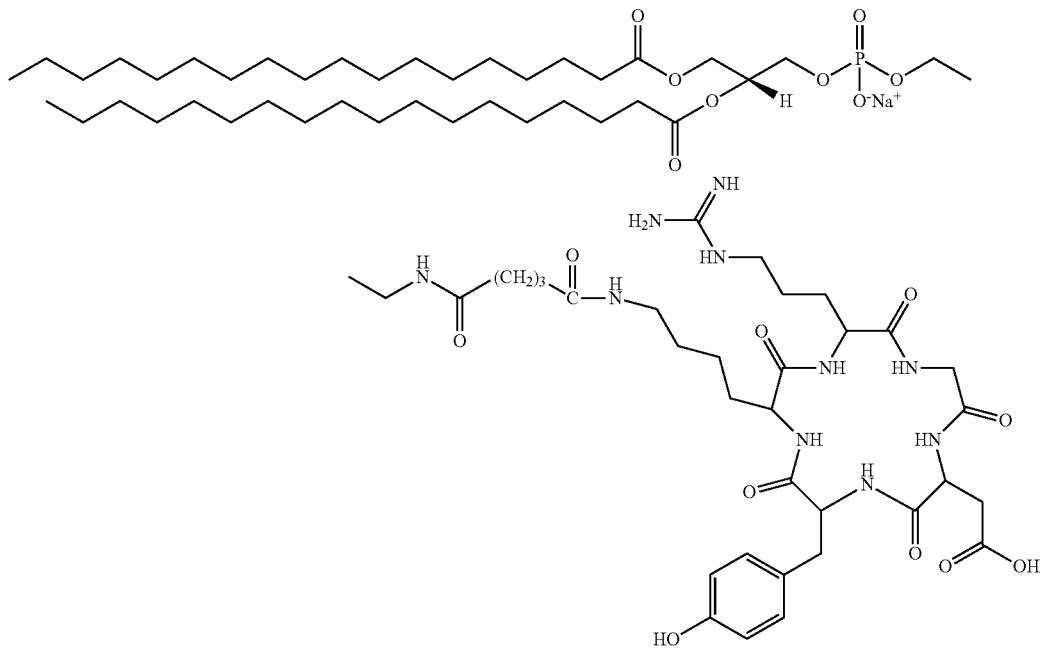

The targeting moiety may be a DSPE-cRGDYK molecule, or any phospholipid that is connected with a cRGDYK moiety itself or connected with a cRGDYK moiety through a linker such as —CO—(CH$_2$)$_3$—(CO)—. The linker may contain a PEG moiety. The phospholipid may be one or more fatty acid esters of C12 to C24. When the linker contains PEG, for example, the targeting moiety may be bound to a lipid molecule (e.g., phospholipid modified with a hydrophilic polymer), existing in the form of DSPE-PEG-cRGDYK. For example, it may be in the form of DSPE-PEG2000-cRGDYK as represented by the following Chemical Formula 2.

[Chemical Formula 2]

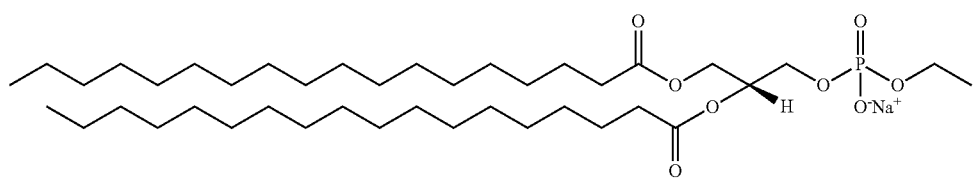

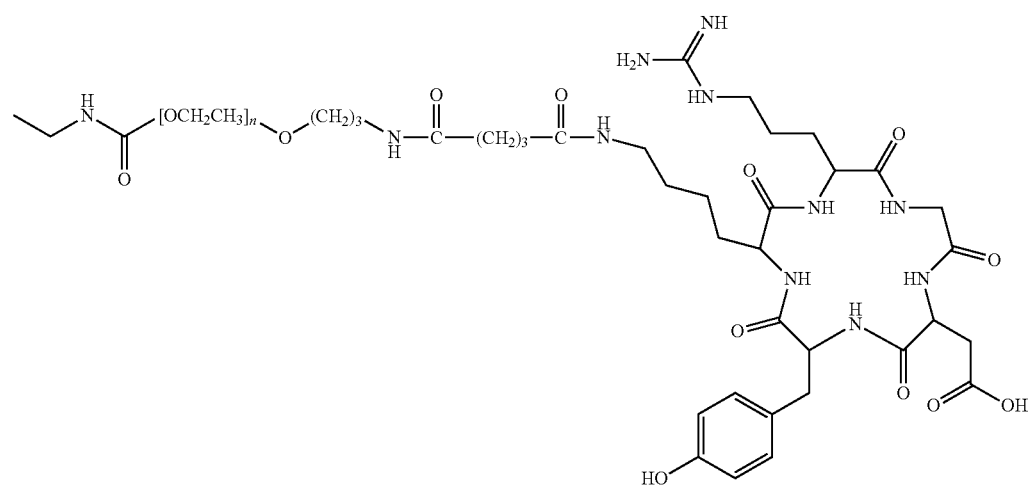

For use in targeting, the peptide (cRGDYK) is an isolated peptide which is 60 amino acids or less (e.g., 2 to 60 amino acids) in length with an amino acid sequence selected from among CRGRRST (SEQ ID NO: 8), CRSRKG (SEQ ID NO: 9), and CKAAKNK (SEQ ID NO: 10). The peptide may selectively home to a premalignant pancreatic vasculature, a malignant pancreatic vasculature, or a pancreatic tumor cell.

For example, the targeting moiety may be linked to the hydrophilic polymer (e.g., PEG) with which the lipid is modified to form a lipid derivative (e.g., DPPC-PEG or DSPE-PEG).

The targeting moiety may be contained in an amount of 0.01 to 10 mol %, based on the amount of moles of the lipid exclusive of the targeting moiety.

The liposomes may be unilamellar vesicles (SUV) or multivesiclular vesicles, with a diameter ranging from about 50 nm to about 500 nm, for example, from about 50 nm to about 400 nm, from about 50 nm to about 300 nm, from about 50 nm to about 200 nm, from about 100 nm to about 500 nm, from about 100 nm to about 400 nm, from about 100 nm to about 300 nm, or from about 100 nm to about 200 nm.

According to one embodiment, the liposome may include a phospholipid, a thermosensitive peptide conjugated to a moiety including a hydrophobic group, a phospholipid derivative derivatized with a hydrophilic polymer, cholesterol, and a cationic lipid (e.g., DPTAP, DOTAP, or a lipid conjugate in which a cationic amino acid is conjugated to a fatty acid). Each component is as described above.

In one embodiment, the phospholipid may be DPPC or a mixture of DPPC and DSPC. In the phospholipid, a molar ratio of DPPC:DSPC may be 1:0 to 0.5, for example, 1:0.1 to 0.5.

In the elastin-like polypeptide conjugated to a moiety including a hydrophobic group, the moiety including a hydrophobic group may be an acyl group and the elastin-like polypeptide has (VPGXG)n or (GVPGX)m, wherein X is an amino acid except proline and n or m is an integer of 1 or greater. X may be valine or alanine. n may be an integer of 1 to 12 or 2 to 12, and m may be an integer of 1 to 12 or 2 to 12. The ELP conjugated to a moiety including a hydrophobic group may be stearoyl-(GVPGX)$_{2-6}$. The terminal carboxyl group of stearoyl-(GVPGX)2-6 may be blocked or not. The blocking may be achieved by forming an amide bond between a carboxyl group and an amino group (e.g., ammonia). The phospholipid derivative derivatized with a hydrophilic polymer may be DPPC-PEG or DSPE-PEG. The PEG may have a molecular weight of 180 to 50,000 Da. The cationic lipid may be DPTAP, DOTAP, or stearic acid-(arginine)$_n$ (n is 3, 6, or 9). The lipid bilayer stabilizing agent may be cholesterol.

The liposomes according to one embodiment of the present invention may have a phase transition temperature of about 10° C. to about 70° C., for example, from about 10° C. to about 60° C., from about 10° C. to about 55° C., from about 10° C. to about 45° C., from about 20° C. to about 60° C., from about 20° C. to about 55° C., from about 30° C. to about 55° C., from about 30° C. to about 45° C., from about 35° C. to about 45° C., from about 38 to about 45° C., from about 39° C. to about 45° C., from about 38° C. to about 42° C., or from about 39° C. to about 42° C. The phase transition temperature may be determined by various factors including the carbon chain length of the primary lipid, the number of unsaturated bonds, lipid mixtures, and combinations thereof. For example, a liposome constructed from a mixture of DPPC and DSPC exhibits a higher phase transition temperature than does a liposome consisting of DPPC alone, because the phase transition temperature of DSPC is higher than that of DPPC. The liposome may be in a gel phase at room temperature.

Another embodiment provides a pharmaceutical composition for the delivery of an anionic drug, including the liposome and the anionic drug. In the pharmaceutical composition, the anionic drug may be entrapped within the inner space of the liposome and/or the interior of the lipid bilayer.

So long as it is negatively charged, any drug, such as an anti-inflammatory agent, an anti-cancer agent, or a nucleic acid, may be used in the present invention. As the anionic drug, a chemical drug having a functional group selected from the group consisting of carboxylate groups (e.g., monocarboxylate, dicarboxylate, tricarboxylate, and multi-carboxylate), sulfate groups, citrate groups, phosphate groups, and phosphorylated functional groups, or a nucleic acid selected from the group consisting of siRNA, oligodi-oxynucleotide (ODN), and DNA may be employed. Examples of the chemical drug available for use as an anionic drug include, but are not limited to, calcein (model drug) and methotrexate (MTX; decarboxylate drug). Among the nucleic acids useful in the present invention are oligonucleotides, microRNA, DNA, non-coding RNA, and siRNA.

The anionic drug forms a complex with a cationic lipid, a constituent of the liposome, by electrostatic interaction, and the resulting anionic drug-associated cationic lipid forms a liposome, together with other constituents, with the anionic drug entrapped within the inner space of the liposome and/or the interior of the lipid bilayer.

In order to facilitate this entrapment, the liposome may have a positive potential. This positive potential may be attributed to the cationic lipid. For example, the zeta potential of the liposome in pure water may range from 1 to 70 mV, for example, from 1 to 50 mV, or from 1 to 45 mV, but is not limited thereto. So long as it guarantees an electrostatic interaction with an anionic drug, any zeta potential may be permitted.

The pharmaceutical composition for delivering an anionic drug may further include a pharmaceutically acceptable carrier and/or diluent. The pharmaceutically acceptable carrier or diluent may be well known in the art. The carrier or diluent may be selected from the group consisting of water, for example saline or sterile water, Ringer's solution, buffered saline, a dextrose solution, a maltodextrose solution, glycerol, ethanol, and combinations thereof.

The structure of the liposome is as described above. The liposomes may be dispersed in an aqueous medium. The aqueous medium may include physiological saline or PBS.

The anionic drug may be entrapped within the inner space of the liposome. Alternatively, the anionic drug may be entrapped in the lipid bilayer of the liposome (a region where the hydrophobic tails are positioned). The liposome may have a phase transition temperature of 38° C. to 45° C. or from 39° C. to 45° C. The liposome may be in a gel phase at room temperature.

If the pharmaceutical composition for delivering an anionic drug is heated to higher than the phase transition temperature of the lipid bilayer, the liposome is destroyed with the transition of the lipid bilayer into a liquid phase, triggering the release of the entrapped anionic drug. Accordingly, the composition may be allowed to release the drug specifically at a target site by controlling the temperature at the target site.

Figure 1:
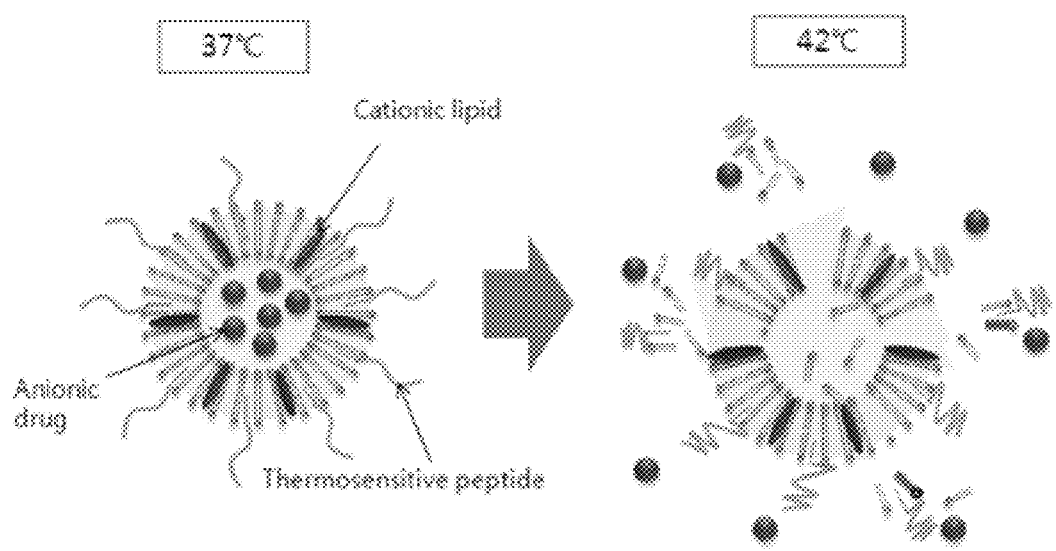
FIG. 1 is a schematic illustrating the drug release mechanism of a pharmaceutical composition including a typical anionic drug.
Figure 2:
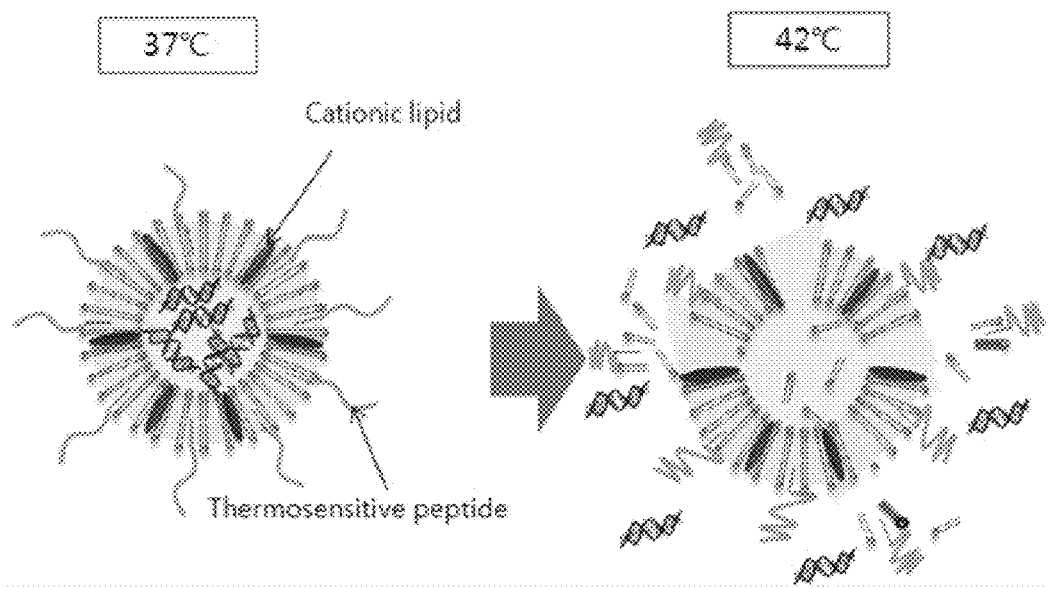
FIG. 2 is a schematic illustrating the drug release mechanism of a pharmaceutical composition including siRNA as an anionic drug.
Figure 3A:
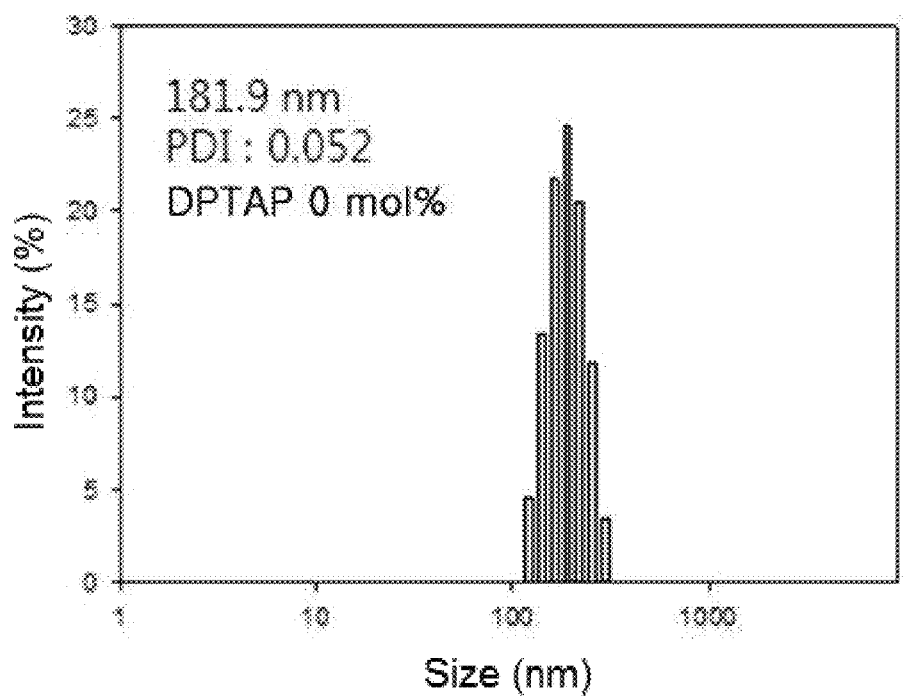
Figure 3C:
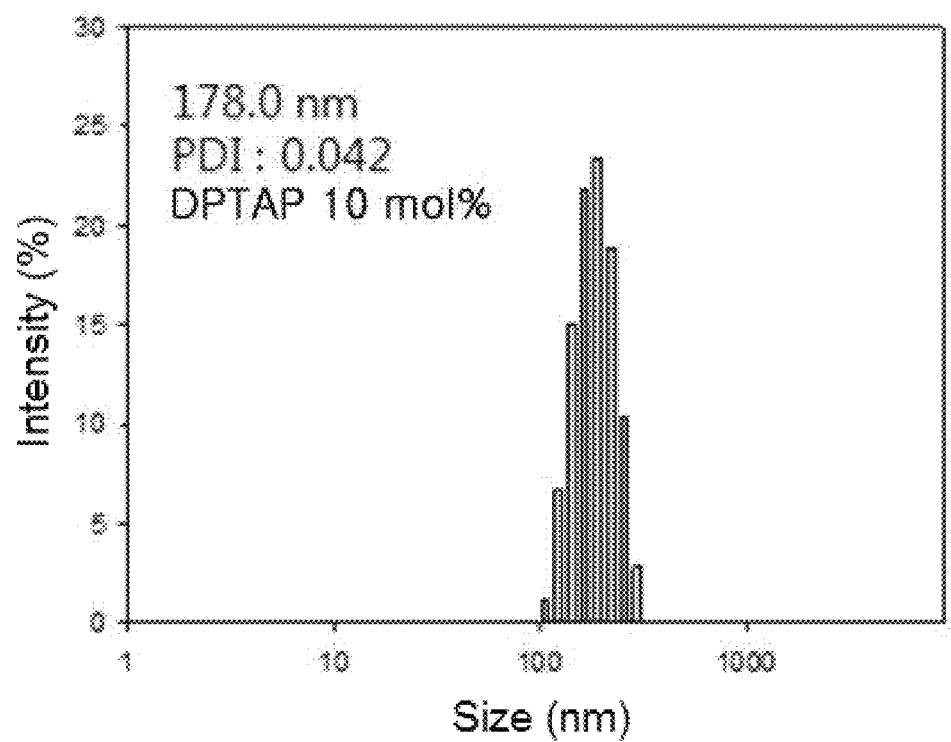
Figure 3D:
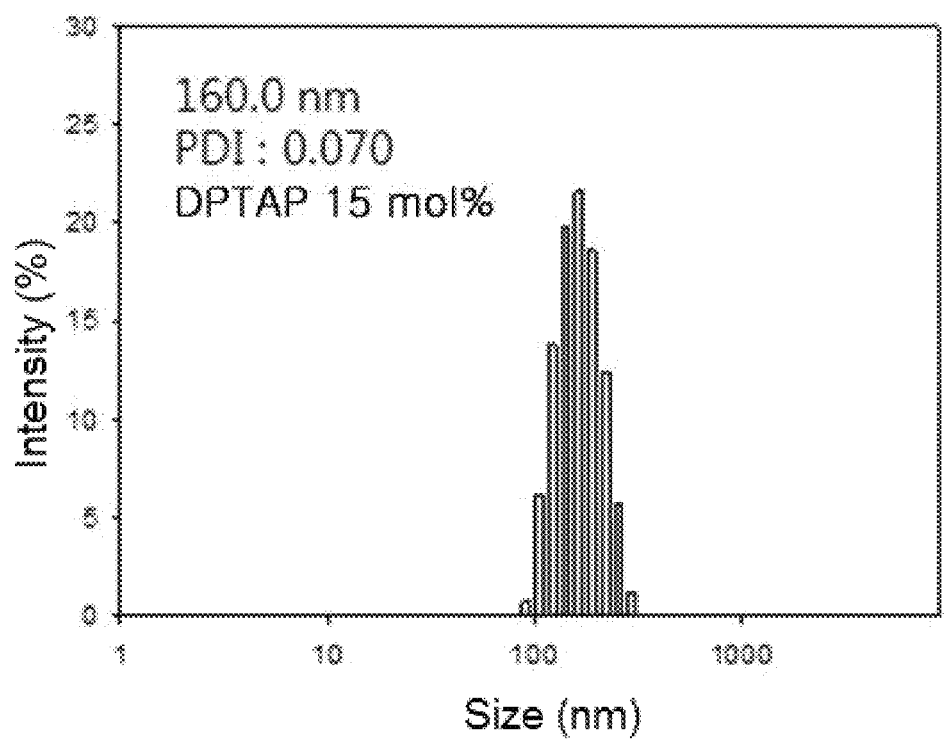
Figure 4A:
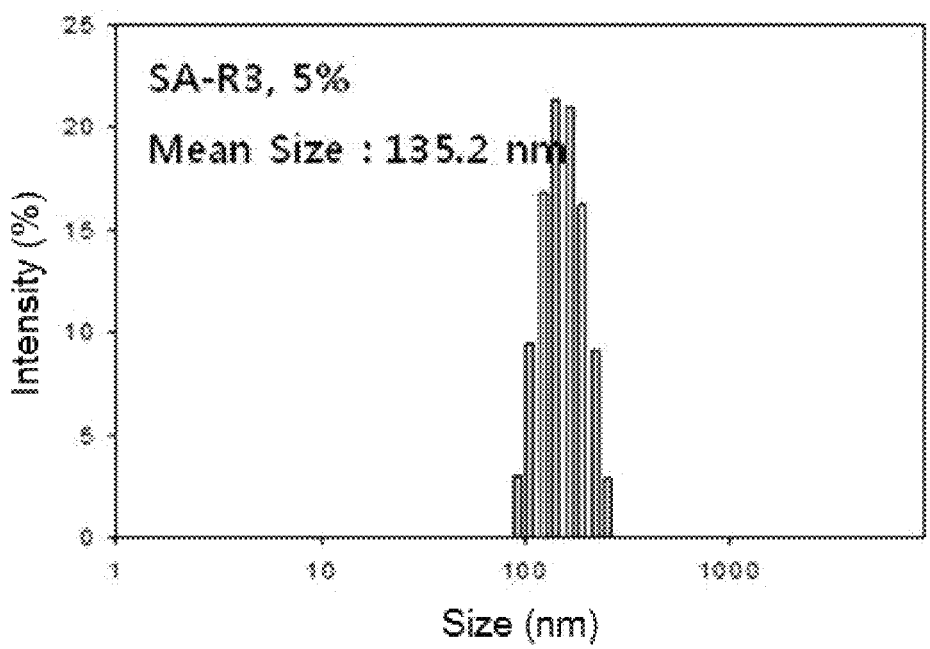
FIGS. 4A, 4B, 4C, and 4D are graphs showing the size distributions of the liposomes (DPPC/SA-(R)$_3$/DSPE-PEG/cholesterol/SA-V3-NH$_2$, cationic model drug: calcein) according to the contents of SA-(R)$_3$ or SA-(R)$_4$ in phospholipid+SA-(R)$_3$ or phospholipid+SA-(R)$_4$ (FIG. 4A: 5 mol % SA-(R)$_3$.
Figure 4B:
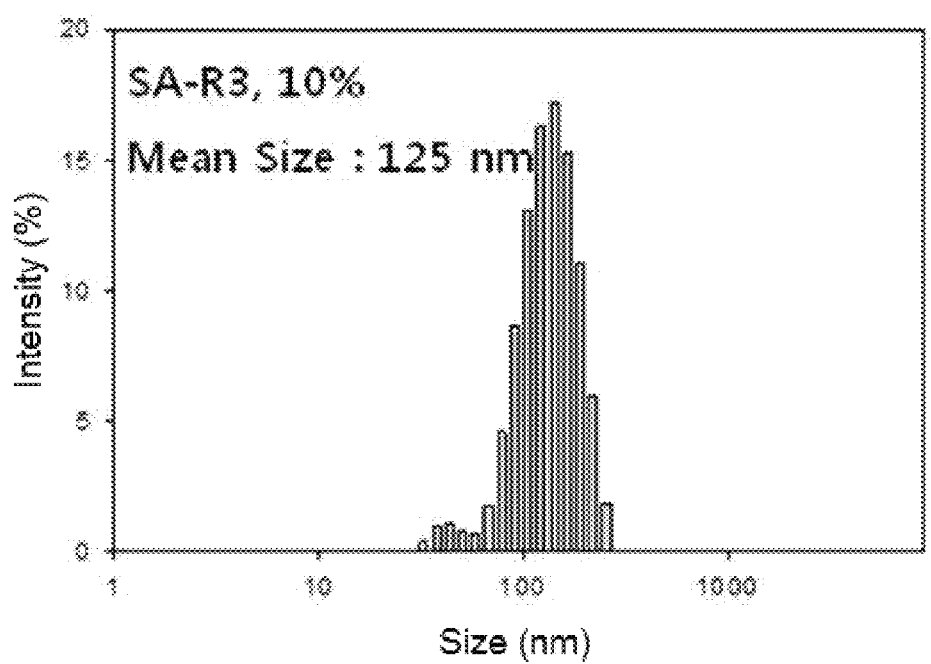
Figure 4C:
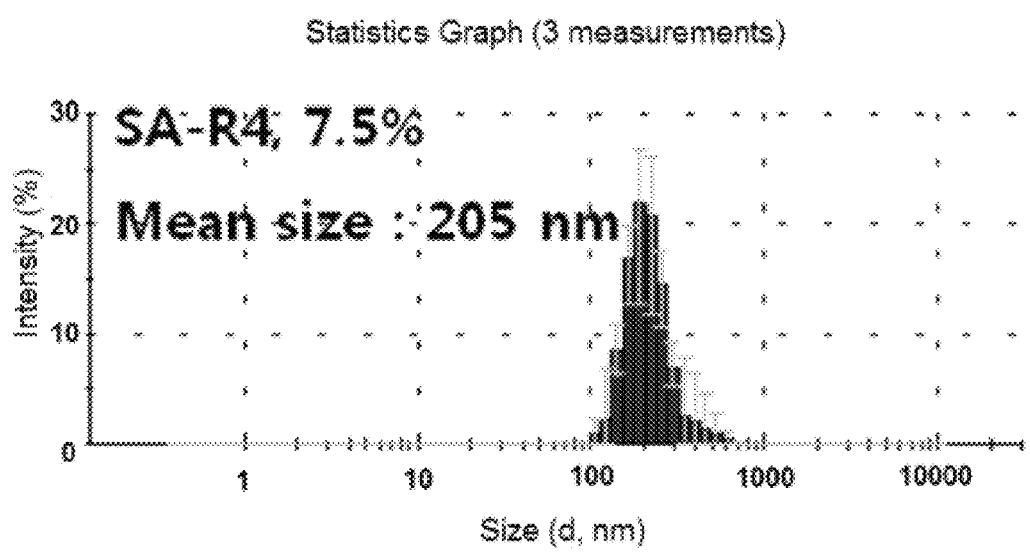
Figure 4D:
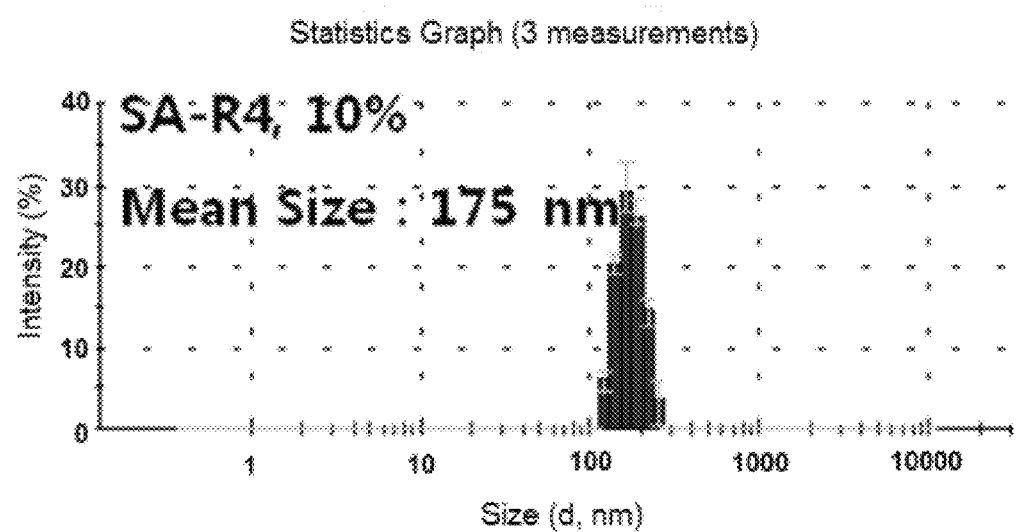

The mechanism by which the pharmaceutical composition releases an anionic drug is schematically illustrated in FIGS. 1 and 2 (FIG. 1: anionic drug, FIG. 2: siRNA as an anionic drug).

The liposomes may be constructed by hydration and/or extrusion. Upon hydration, the anionic drug can be entrapped within the liposome.

Another embodiment provides a method for delivering an anionic drug, including administering the pharmaceutical composition to a patient. The method may further include a step of heating a lesion (target site). The heating step may be conducted prior to, subsequent to or simultaneously with the administering step in consideration of the patient's condition, the property and state of the lesion, and a therapeutic effect. The term "lesion" refers to a region in which a disease or a resultant symptom occurs, for example, a tumor site (e.g., solid tumor), an inflammatory site, etc. In addition, it may be a target site to which the anionic drug entrapped to the pharmaceutical composition is applied.

As described above, when the pharmaceutical composition for delivering an anionic drug is heated to higher than the phase transition temperature of the lipid bilayer, the liposome is destroyed with the transition of the lipid bilayer into a liquid phase, performing the release of the entrapped anionic drug. Accordingly, if the lesion is heated to higher than the phase transition temperature of the lipid bilayer by inflammation or by artificially heating, the pharmaceutical composition of the present invention can release the anionic drug specifically to the lesion only. Thus, the method for delivering an anionic drug is very useful for delivering the anionic drug specifically to the lesion (target site) in the body.

The liposome contained in the pharmaceutical composition for delivering an anionic drug may have a phase transition temperature of about 39° C. to about 45° C.

The administration may be oral or parenteral, with preference for oral administration. The parenteral administration, for example, may be intravenous, intradermal, intramuscular, intracavity (abdominal, articular, ocular cavityor eye), or direct injection. The direct injection may involve injecting directly into a lesion such as a tumor site. The liposomes may be administered intravenously and thereby brought to the target site such as a tumor site by blood flow. The target site may have a leaky property.

The subject may be a mammal, particularly, a human who is in need of treatment with the anionic drug contained in the pharmaceutical composition of the present invention.

The heating may be performed by direct heat transfer, for example, contacting a lesion (target site) with a hot or heating medium (e.g., hot water in a tub) or a heat transfer device containing the hot or heat-generating medium (e.g., hot pack), irradiating ultrasound, e.g., high intensity ultrasound focused at a target site, applying a magnetic field, e.g., an amplified magnetic field (AMF), and applying microwaves and/or radiofrequency. The heating is to maintain the lesion at a temperature of about 35° C. to about 45° C., from about 38° C. to about 45° C., from about 39° C. to about 45° C., from about 38° C. to about 42° C., or from about 39° C. to about 42° C.

Still another embodiment provides a kit for the delivery of an anionic drug, including the pharmaceutical composition for delivering an anionic drug, and a heating means.

As for the pharmaceutical composition used in the kit, its constitutional elements are as described above. The heating means is designed to apply heat to a lesion, that is, a target site of the anionic drug so as to increase the temperature of the lesion to higher than the phase transition temperature of the lipid bilayer of the liposome contained in the pharmaceutical composition. Any conventional heating means may be used. For example, the heating means may be a hot or heating medium (e.g., hot water), a heat transfer device containing the hot or heat-generating medium (a device designed to slowly release heat from the hot or heating medium to a target site at a temperature applicable to the body, for example, a hot pack), or a machine for generating an ultrasound, a magnetic field, a microwave and/or a radio frequency.

According to one embodiment, a method of preparing the liposome is provided. The method may include admixing a lipid bilayer, a thermosensitive peptide conjugated to a moiety comprising a hydrophobic group, and a cationic lipid. The step of admixing may be performed by dissolving the lipid bilayer, the thermosensitive peptide conjugated to a moiety comprising a hydrophobic group, and the cationic lipid in a suitable solvent. The suitable solvent may be at least one selected from, but not be limited to, the group consisting of water, alcohol (e.g., C1-C10 linear or branched alcohol), chloroform, and the like. The method may further include a step of adding an anionic drug to a mixture of the lipid bilayer, the thermosensitive peptide conjugated to a moiety comprising a hydrophobic group, and the cationic lipid, or admixing an anionic drug with the lipid bilayer, the thermosensitive peptide conjugated to a moiety comprising a hydrophobic group, and the cationic lipid. The kinds and ratio of the lipid bilayer, the thermosensitive peptide conjugated to a moiety comprising a hydrophobic group, the cationic lipid, and the anionic drug are as described above.

Structured to feasibly entrap anionic drugs therein and to deliver the drugs selectively to target sites in addition to prolonging the in vivo half-life period of the entrapped anionic drugs and promoting the cellular uptake of the entrapped anionic drugs, the cationic, thermosensitive liposome of the present invention can be applied to the delivery of various anionic drugs, for example, anti-inflammatory agents, anti-cancer agents, nucleic acids, etc.

Hereafter, the present invention will be described in detail by examples. The following examples are intended merely to illustrate the invention and are not construed to restrict the invention.

EXAMPLES

Example 1

Construction of Liposome

Unilamellar vesicle liposomes were constructed using a mixture of phospholipid+cationic lipids, a lipid derivative derivatized with a hydrophilic polymer, a lipid bilayer stabilizing agent, and an elastin-like polypeptide conjugated to a moiety including a hydrophobic group at a molar ratio of 55:2:10:0.55.

In detail, 1,2-dipalmitoyl-sn-glycero-3-phosphocholine (DPPC) and 1,2-distearoyl-sn-glycero-3-phosphocholine (DSPC) were used as the phospholipid, DPTAP, stearic acid-(arginine)$_3$, stearic acid-(arginine)$_4$, stearic acid-(arginine)$_6$, or stearic acid-(arginine)$_9$ as the cationic lipid, 1,2-distearoyl-sn-glycero-3-phosphoethanolamine-N-[methoxy (polyethylene glycol)-2000 (ammonium salt)] (DSPE-PEG; PEG average molecular weight: 2000) or DSPE-PEG-cRGD (cyclic RGD) as the hydrophilic polymer, and stearoyl-VPGVG VPGVG VPGVG-NH$_2$ (hereinafter referred to as "SA-V3-NH2") as the moiety including a hydrophobic group-conjugated elastin-like polypeptide.

Based on 100 moles of phospholipid+cationic lipid, the phospholipids DPPC and DSPC, and the cationic lipid (DPTAP, stearic acid-(arginine)$_3$[SA-(R)$_3$], stearic acid-(arginine)$_3$[SA-(R)$_4$], stearic acid-(arginine)$_6$[SA-(R)$_6$], or stearic acid-(arginine)$_9$[SA-(R)$_9$]) were used at a molar ratio of 75:25:0 (control), 70:25:5, 67.5:25:7.5, or 60:25:10 (DPPC:DSPC:cationic lipid).

In this regard, SA-V3-NH$_2$ was dissolved in ethanol while DPPC, DSPC, DSPE-PEG or DSPE-PEG-cRGD, and cholesterol were dissolved in chloroform. Methanol was used as a solvent for dissolving the cationic lipid. The ethanol solution was mixed with the chloroform and the methanol solution in a round bottom flask, followed by evaporating the solvents at room temperature using a rotary evaporator to form a lipid thin layer on the internal wall of the flask.

Subsequently, physiological saline (pH 7.3-7.6) was added to the flask to hydrate the lipid thin layer. The hydrated solution was filtered through a polycarbonate membrane with a pore size of 100 nm to obtain unilamellar vesicle liposomes.

Example 2

Construction of Anionic Drug-Entrapped Liposome

The lipid thin layer formed on the internal surface of the flask in Example 1 was hydrated at room temperature with a 200 mM solution of the aqueous fluorescent molecule calcein in physiological saline (pH 7.3-7.6). The hydrated solution was filtered at room temperature through a polycarbonate membrane with a pore size of 100 nm to obtain unilamellar vesicle liposomes. The resulting liposome solution was entrapped to a PD-10 (GE Healthcare) desalting column, and then eluted with physiological saline to remove the calcein which remained untrapped. As a result, liposomes in which calcein were entrapped were constructed. The constructed liposomes were found to have an average diameter of about 100 to 200 nm as measured by Zeta-sizer instrument (Zetasizer nano-ZS, Malvern inst.).

MTX (methotrexate) instead of calcein was entrapped. In this regard, the hydration was conducted with 1 mg/ml MTX before filtration through a 100 nm polycarbonate membrane. MTX-entrapped liposomes and free MTX were isolated from the resulting liposome solution by gel filtration column chromatography (Sepadex G-50) to purify MTX-entrapped liposome. As a result, liposomes with MTX entrapped in the aqueous interior thereof were obtained.

For entrapping siRNA, the liposomes which were prepared by hydrating at room temperature with physiological saline and filtering through a polycarbonate membrane with a pore size of 100 nm were complexed with siRNA. GFP siRNA (sense 5'-AAC UUC AGG GUC AGC UUG CdTdT-3' (SEQ ID NO: 11-dTdT), antisense 5'-GCA AGC UGA CCC UGA AGU UdTdT-3' (SEQ ID NO: 12-dTdT)) or VEGR siRNA (sense 5'-GGA GUA CCC UGA UGA GAU CdTdT-3' (SEQ ID NO: 13-dTdT), antisense 5'-GAU CUC AUC AGG GUA CUC CdTdT-3' (SEQ ID NO: 14-dTdT)) was used.

FIGS. 3A to 3D are graphs showing the size distributions of the liposomes (DPPC/DPTAP/DSPE-PEG/cholesterol/SA-V3-NH$_2$, anionic model drug: calcein) according to the content of DPTAP in phospholipid+DPTAP. FIG. 4A to 4D are graphs showing the size distribution of the liposomes (DPPC/SA-(R)$_3$/DSPE-PEG/cholesterol/SA-V3-NH$_2$, cationic model drug: calcein) according to the contents of SA-(R)$_3$ or SA-(R)$_4$ in phospholipid. As can be seen in FIGS. 3A to 4D, the liposomes had relatively constant average diameters irrespective of the presence or absence and the amount of cationic lipids, which indicate that cationic lipids have no influences on the size distribution of the liposomes.

Example 3

Zeta Potential of Liposome

The liposomes constructed in Example 1 were measured for zeta potential. In this regard, the surface potentials of the liposomes were measured using Zeta-sizer (Zetasizer nano-ZS, Malvern inst.) and Zeta cell (DTS-1060C). In the Zeta cell (DTS-1060C) was placed 600 µl of a liposome sample, with care not to produce bubbles, and the cell was entrapped to the Zeta-sizer instrument to measure a Zeta potential (mv).

Zeta potential values measured according to the content of DPTAP in the phospholipid+DPTAP of the liposomes (DPPC/DSPC/DPTAP/DSPE-PEG/cholesterol/SA-V3-NH$_2$) are summarized in Table 1 below while Table 2 shows zeta potential values measured according to the content of SA-(R)$_3$ in the phospholipid+SA-(R)$_3$ of the liposomes (DPPC/DSPC/SA-(R)$_3$/DSPE-PEG-cRGD/cholesterol/SA-V3-NH$_2$). In addition, zeta potential values measured according to the content of SA-(R)$_4$ in the phospholipid+SA-(R)$_4$ in the liposomes (DPPC/DSPC/SA-(R)$_4$/DSPE-PEG-cRGD/cholesterol/SA-V3-NH2) are given in Table 3, below.

TABLE 1

Zeta Potential According to DPTAP Content of Liposome

| (DPPC/DSPC/DPTAP/DSPE-PEG/cholesterol/SA-V3-NH$_2$) Content of DPTAP in Phospholipid + DPTAP (mol %) | Zeta potential (mV) |
| --- | --- |
| 0 (Control) | −61.6 |
| 5 | 19.0 |
| 10 | 39.2 |
| 15 | 42.0 |

TABLE 2

Zeta Potential According to SA-(R)$_3$ Content of Liposome
(DPPC/DSPC/SA-(R)$_3$/DSPE-PEG-cRGD/cholesterol/SA-V3-NH$_2$)

| Content of SA-(R)$_3$ in Phospholipid + SA-(R)$_3$ (mol %) | Zeta potential (mV) |
| --- | --- |
| 0 (Control) | −23.4 |
| 5 | 44.6 |
| 10 | 49.2 |

TABLE 3

Zeta Potential According to SA-(R)$_4$ Content of Liposome (DPPC/DSPC/SA-(R)$_4$/DSPE-PEG/cholesterol/SA-V3-NH$_2$)

| Content of SA-(R)$_4$ in Phospholipid + SA-(R)$_4$ (mol %) | Zeta potential (mV) |
| --- | --- |
| 0 (Control) | −53.8 |
| 5 | 33.8 |
| 10 | 42.8 |

As can be seen in Tables 1 to 3, the controls, which were free of cationic lipids, could not form a complex with an anionic drug through electrostatic attraction because they had negative zeta potentials, whereas the liposomes of the present invention exhibited positive zeta potentials thanks to the presence of cationic lipids so that they could form a complex with anionic drugs and thus entrap the drugs therein. The zeta potential of the liposomes of the present invention increased in a dose-dependent manner with an increase in the content of cationic lipids. Throughout the content range of cationic lipids, in addition, the zeta potential of the liposome was maintained at a level of 1 to 50 mV, which allows the liposomes to complex with anionic drugs, without evoking toxicity in vivo. Therefore, the liposomes of the present invention are biocompatible and can effectively entrap anionic drugs therein.

Example 4

Release Behavior of Anionic Drug According to Content of Cationic Lipid

The anionic drug-entrapped liposomes (DPPC/DPTAP/DSPE-PEG/cholesterol/SA-V3-$NH_2$, anionic model drug: calcein) constructed in Example 2 were analyzed for the drug release behavior of the anionic model drug (calcein) according to the content of the cationic lipid (DPTAP). Temperature-dependent release profiles of drugs from the liposomes were evaluated by measuring the amount of calcein released into the surrounding solution from the aqueous interior of the liposomes after incubation at 25° C. to 55° C. in physiological saline. After incubation, the solution was suitably diluted, and measured for fluorescence intensity at an excitation wavelength ($\lambda$ex)=485 nm and an emission wavelength ($\lambda$em)=635 nm to determine the amount of calcein released from the liposomes. The fluorescence intensity detected according to incubation at a certain temperature was calculated as percentages by comparison with the total release of entrapped material obtained after the disruption of the liposomes with 1% Triton X-100 (DMSO).

FIG. 5 is a graph showing the temperature release profiles of calcein from the liposomes constructed from mixtures of DPPC/DSPC/DPTAP, DSPE-PEG, cholesterol and SA-V3-NH2-$NH_2$ at respective molar ratios of 55 (75/25/0):2:10:0.55, 55 (70/25/5):2:10:0.55, 55 (65/25/10):2:10:0.55, 55 (60/25/15):2:10:0.55, and 55 (55/25/5):2:10:0.55 in Example 4.

As can be seen in FIG. 5, the liposomes containing DPTAP was less prone to drug release at around the phase transition temperature than was the control free of DPTAP. This data indicates that the liposomes containing DPTAP can release the entrapped drug in a controlled manner by preventing the drug from bursting in an early stage.

Figure 6:
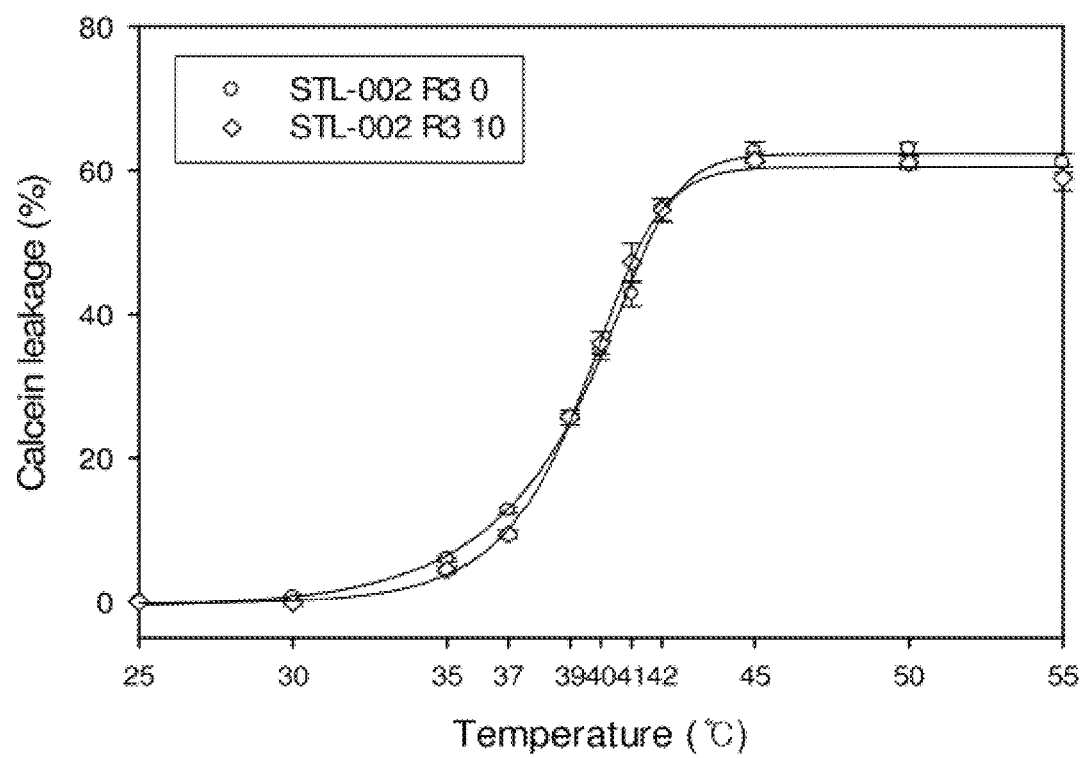
FIG. 6 is a graph showing the temperature release profiles of calcein from the liposomes (DPPC/DSPC/DSPE-PEG/cholesterol/SA-V3-NH$_2$ or DPPC/DSPC/SA-(R)$_3$/DSPE-PEG/cholesterol/SA-V3-NH$_2$, anionic model drug: calcein).

FIG. 6 is a graph showing the temperature release profiles of calcein from the liposomes constructed from mixtures of DPPC/DSPC/SA-$(R)_3$, DSPE-PEG, cholesterol and SA-V3-$NH_2$ at respective molar ratios of 55 (75/25/0):2:10:0.55, and 55 (65/25/10):2:10:0.55 in Example 4. In this case, the phase transition temperature was observed to remain almost constant.

Example 5

Entrapment of Anionic Drug

MTX-entrapped liposomes were constructed from mixtures of DPPC/DSPC/SA-$(R)_3$, DSPE-PEG:cholesterol and SA-V3-$NH_2$ at molar ratios of 55(75/25/0):2:10:0.55 and 55(65/25/10):2:10:0.55 according to the disclosure of Example 2. The amount of MTX entrapped in the liposomes was analyzed by HPLC (Waters e2695 separation module, detector Waters2489). Free MTX solutions were prepared at various concentrations (0.003 mg/ml to 0.384 mg/ml) (standard curve solutions). Separately, MTX-entrapped liposomes were dissolved in DMSO (final concentration 50%, v:v=1:1) (sample solution to be measured). HPLC analysis was performed by eluting the drug with both a 0.1% (v/v) TFA (trifluoroacetic acid) solution in distilled water (A) and a 0.1% (v/v) TFA solution (B) in CAN (acetonitrile) as a mobile phase, followed by absorbance at 303 nm. Peaks characteristic of MTX were observed, indicating that the drug was entrapped inside the liposomes. In addition, a standard curve was drawn by plotting peak areas versus standard MTX concentrations, and the peak areas of the samples were calculated and applied to the standard curve to determine the concentrations of the MTX entrapped.

Figure 7A:
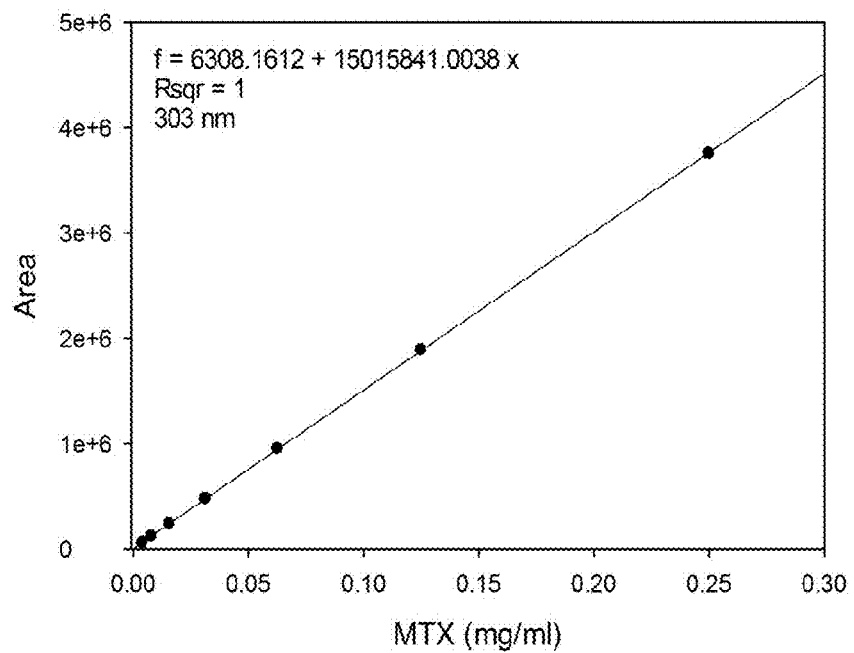
FIG. 7A is a graph showing the free MTX quantification by measuring absorbance at 303 nm as function of the concentration.
Figure 7B:
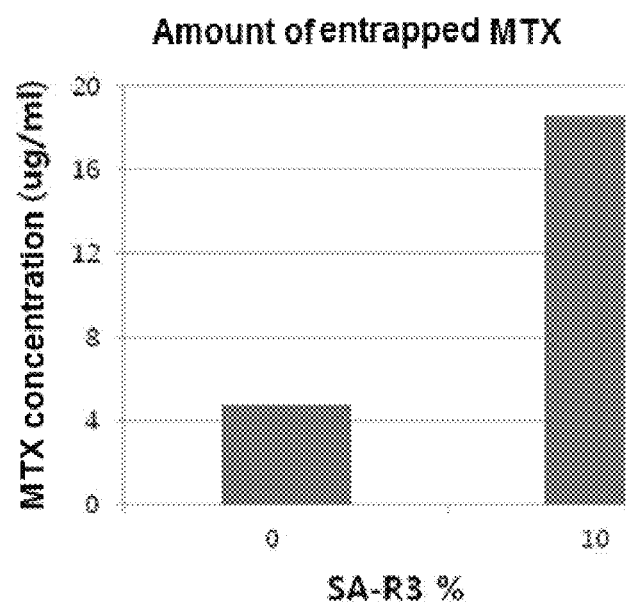
FIG. 7B is a graph showing the amounts of MTX entrapped inside the liposomes (DPPC/DSPC/cholesterol/[SA-V3-NH$_2$] or DPPC/DSPC/SA-(R)$_3$/cholesterol/SA-V3-NH$_2$) by calculating according to the standard curve FIG. 7A.

FIG. 7A is a standard curve plotted from the absorbance at 300 nm detected in various concentrations of free MTX solutions. FIG. 7B is a graph of MTX concentrations in the liposomes which contained the cationic lipid SA-R3 in an amount of 0% and 10% of the primary lipid, respectively. As can be seen in FIGS. 7A and 7B, the amount of entrapped MTX in the liposomes was 4-fold greater when the liposomes contained SA-R3 in an amount of 10% of the primary lipid, compared to the liposomes containing no SA-R3.

Example 6

Gel Retardation Assay for siRNA/Liposome Complexation

Liposomes were constructed from a mixture of DPPC/DSPC/SA-$(R)_3$, DSPE-PEG, cholesterol and SA-V3-$NH_2$ at a molar ratio of 55 (75/25/0):2:10:0.55 or 55 (65/25/10):2:10:0.55 according to the disclosure of Example 1. Separately, liposomes were constructed from a mixture of DPPC/DSPC/SA-$(R)_4$, DSPE-PEG, cholesterol and SA-V3-$NH_2$ at a molar ratio of 55 (67.5/25/7.5):2:10:0.55 or 55 (65/25/10):2:10:0.55. The liposomes were mixed with siRNA in such a manner that at weight ratios of SA-$(R)_3$/siRNA or SA-$(R)_4$/siRNA were 3.2, 3.9, 5.2, 6.4, 13, 19, 26, and 32, and the mixture was incubated at room temperature for 30 min. Thereafter, the siRNA was run at 110 V for 20 min on a 2% agarose gel.

Figure 8:
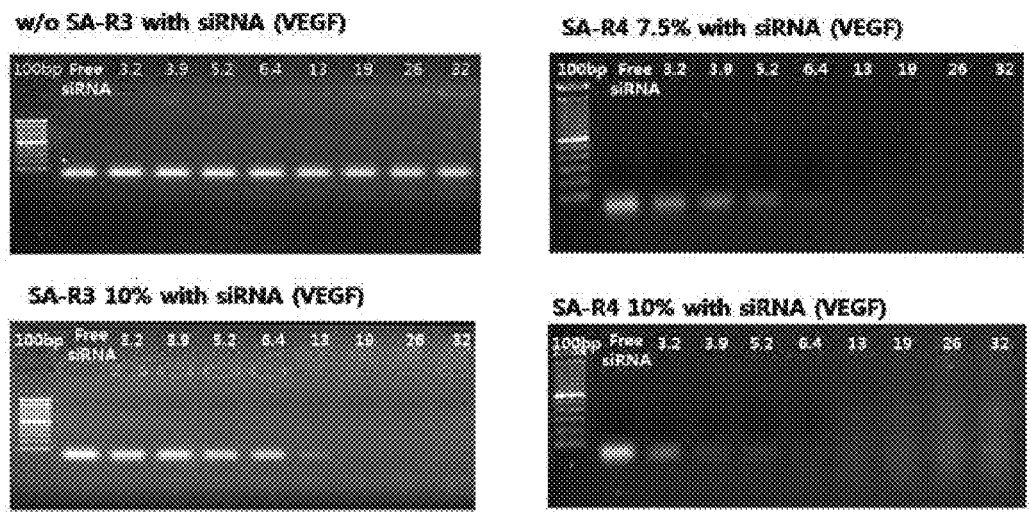
FIG. 8 is a set of photographs showing results of the gel retardation assay of siRNA complexed with liposomes (DPPC/DSPC/DSPE-PEG-cRGD/cholesterol/SA-V3-NH$_2$, DPPC/DSPC/SA-(R)$_3$/DSPE-PEG-cRGD/cholesterol/SA-V3-NH$_2$ or DPPC/DSPC/SA-(R)$_4$/DSPE-PEG/cholesterol/SA-V3-NH$_2$).

FIG. 8 shows results of the gel retardation assay of siRNA complexed with liposomes. As can be seen in FIG. 8, only free siRNA was detected in the liposomes free of cationic lipids, and in the liposomes containing SA-R3 in an amount of 10% of the primary lipid, gel retardation was observed when at a weight ratio of SA-$(R)_3$/siRNA was 13 or higher, indicating that the complexation of siRNA/liposome started to occur from the weight ratio. In addition, when SA-$(R)_4$ was used in an amount of 7.5% and 10% of the primary lipid, siRNA/liposome complexation started to occur from a SA-$(R)_3$/siRNA weight ratio of 6.4 and 5.2, respectively.

Example 7

Cytotoxicity of Empty Liposome

Empty liposomes were constructed from a mixture of DPPC/DSPC/SA-$(R)_3$, DSPE-PEG, cholesterol and SA-V3-$NH_2$ at a molar ratio of 55 (65/25/10):2:10:0.55 in the same manner as in Example 1, and measured for cytotoxicity against MDAMB435 cells. MDAMB-435 cells (ATCC) were seeded at a density of $10^4$ cells/well into 96-well plates and incubated for 24 hrs in DMEM (Dulbecco's modified Eagle's medium) supplemented with 10% (v/v) FBS (Fetal bovine serum) and 1% (w/v) penicillin/streptomycin. After the medium was removed, the MDAMB435 cells were incubated at 37° C. for 24 hrs with various concentrations of the empty liposomes. Then, the cells were incubated for an additional 4 hrs with a CCK-8 (Dojindo) kit, followed by reading absorbance at 450 nm. Cytotoxicity was evaluated by relative ratios of the absorbance.

Figure 9:
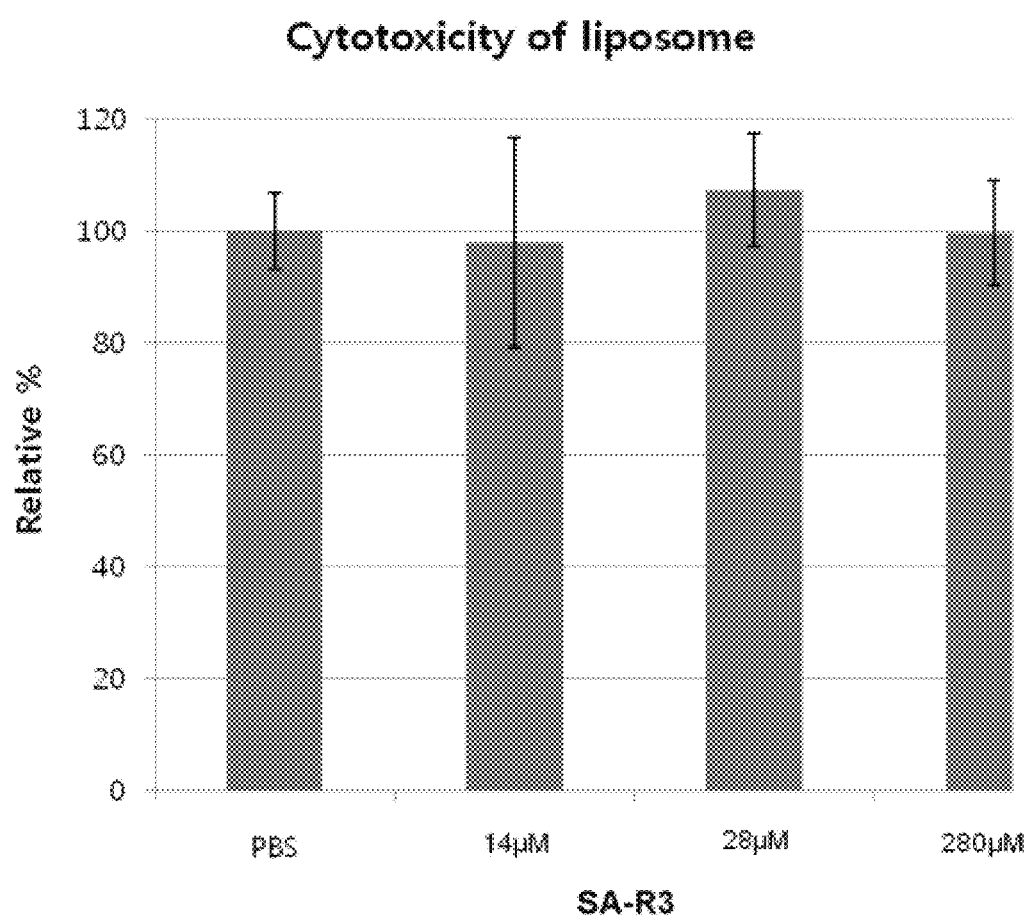
FIG. 9 is a graph showing the cytotoxicity of the empty liposomes (DPPC/DSPC/SA-(R)$_3$/DSPE-PEG/cholesterol/SA-V3-NH$_2$) according to SA-(R)$_3$/siRNA ratio.

FIG. 9 is a graph showing the cytotoxicity of the empty liposomes. The concentrations (μM) of SA-$R_3$ are given on the X-axis in FIG. 9. As is understood from the data of FIG. 9, no cytotoxicity was found even in the liposomes which contained the same amount of SA-$(R)_3$ as in an SA-$(R)_3$/siRNA weight ratio of 13, which induced sufficient complexation between liposomes and siRNA, indicating that liposomes themselves (that is, the carrier itself necessary for siRNA binding) are not toxic at all.

Example 8

Expression of GFP (Green Fluorescence Protein)

Liposomes were constructed from a mixture of DPPC/DSPC/SA-$(R)_3$, DSPE-PEG, cholesterol and SA-V3-$NH_2$ at a molar ratio of 55 (65/25/10):2:10:0.55 according to the disclosure of Example 2, and used in a GFP (Green Fluorescence Protein) expression assay with GFP-overexpressed MDAMB435 cells. MDAMB-435 cells were seeded at a density of $2 \times 10^5$ cells/well into 12-well plates and maintained for 24 hrs in DMEM (Dulbecco's modified Eagle's medium) supplemented with 10% (v/v) FBS (Fetal bovine serum) and 1% (w/v) penicillin/streptomycin. After the medium was removed, the cells were washed twice with PBS, and maintained in a serum-free medium (360 μl/well). The cells were incubated at 37° C. for 4 hrs after a siRNA/liposome complex in which the cationic lipid SA-R3 and siRNA were used at an SA-R3/siRNA weight ratio of 13 was added in an amount of 40 μl/well. In a thermoshaker, the cells were thermally treated at 42° C. for 30 min. Thereafter, the medium was exchanged with a medium supplemented with 10% FBS (2 ml/well), followed by incubation at 37° C. for 48 hrs. Subsequently, the cells were lysed by incubating at 4° C. for 30 min in 1% Triton, with vortexing every 10 min. The cell lysate was at 4° C. and 14,000 rpm for 20 min, and the supernatant was removed, and used for measuring fluorescence intensity at an excitation wavelength ($\lambda$ex)=488 nm and an emission wavelength ($\lambda$em)=525 nm.

Figure 10:
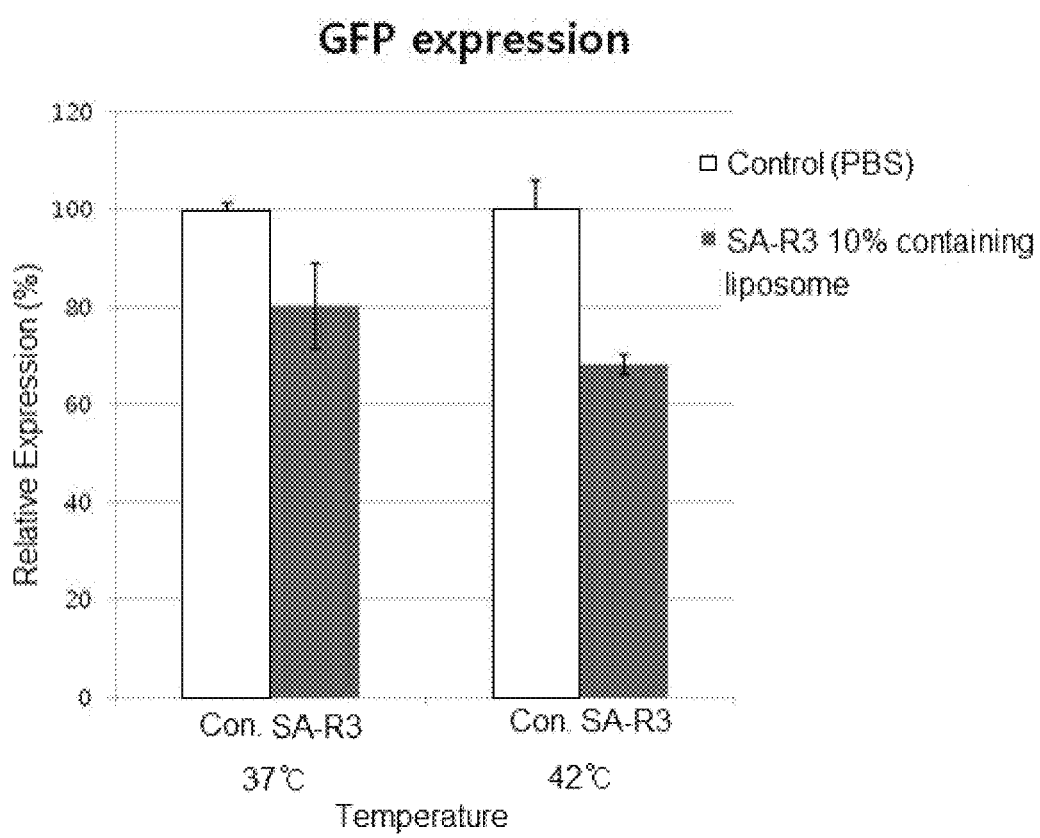
FIG. 10 is a graph showing the inhibitory activity of the liposome (DPPC/DSPC/SA-(R)$_3$/DSPE-PEG/cholesterol/SA-V3-NH$_2$)/siRNA complex against GFP expression according to temperature.

FIG. 10 is a graph showing GFP expression levels in GFP-overexpressed MDAMB435 cells treated with or without a liposome/siRNA complex with a SA-R3/siRNA weight ratio of 13. As can be seen in FIG. 10, the liposome complex was found to suppress protein expression by 20% at 37° C. as GFP was 80% expressed, and by 32% at 42° C. as GFP was 68% expressed.

Example 9

Cytotoxicity Assay

MTX was entrapped to the liposomes which were constructed from a mixture of DPPC/DSPC/SA-$(R)_3$, DSPE-PEG, cholesterol, and SA-V3-$NH_2$ at a molar ratio of 55 (65/25/10):2:10:0.55, in the same manner as in Example 2. HeLa cells (ATCC) were seeded at a density of $1 \times 10^4$ cells/well into 96-well plates and maintained for 24 hrs in DMEM (Dulbecco's modified Eagle's medium) supplemented with 10% (v/v) FBS (Fetal bovine serum) and 1% (w/v) penicillin/streptomycin. After the medium was removed, the cells in each well were treated with 100 μl of the MTX-entrapped liposomes (10.7 μg/ml), and thermally incubated at 37° C. or 42° C. in a thermoshaker. Subsequently, the medium was exchanged with a 10% FBS medium (2 ml/well), and the cells were incubated at 37° C. for 24 hrs. Cells were observed under a microscope.

Figure 11A:
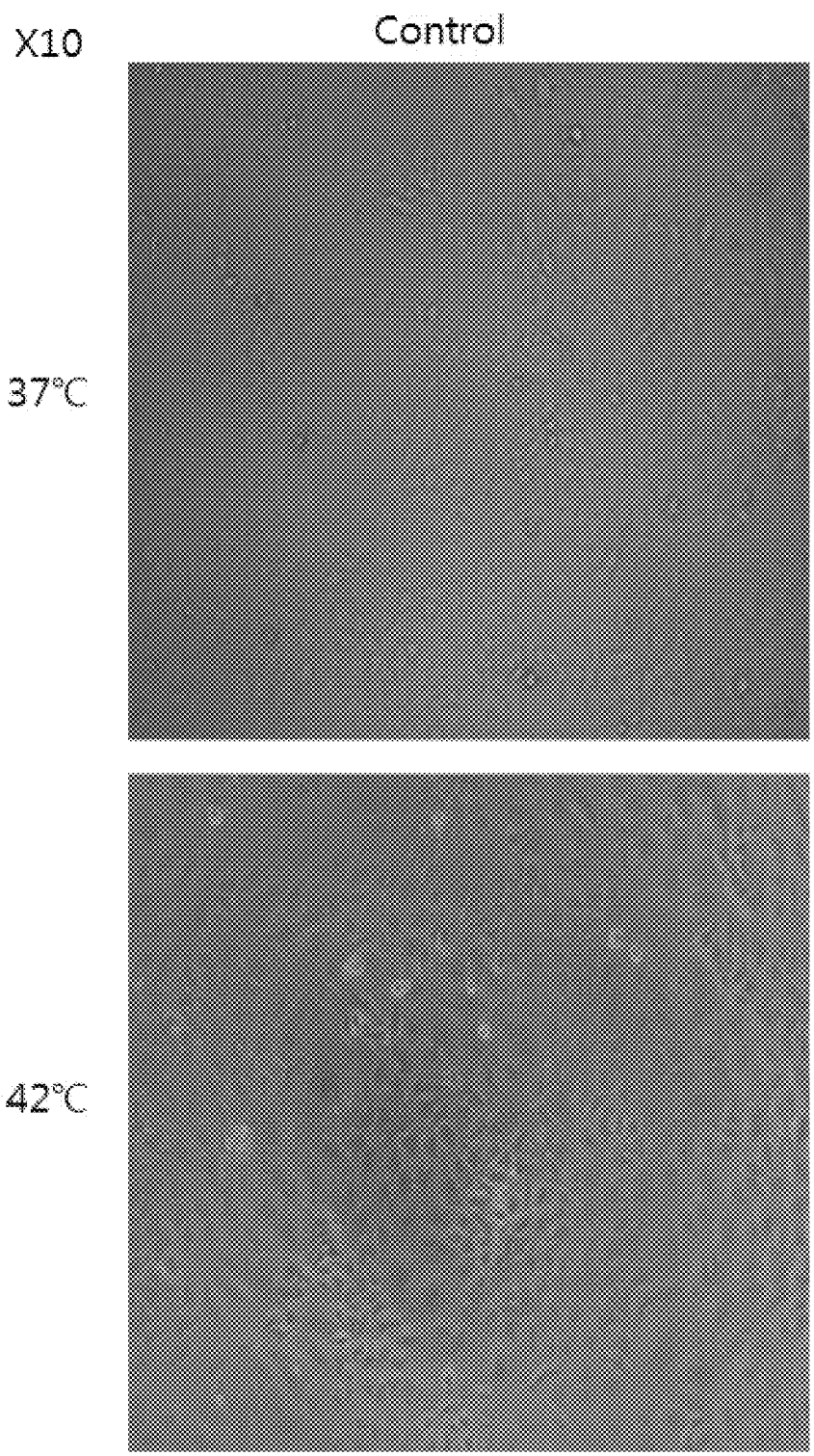
FIGS. 11A and 11B illustrate sets of images of the cells non-treated (control) (11A) and treated with liposomes (11B).
Figure 11B:
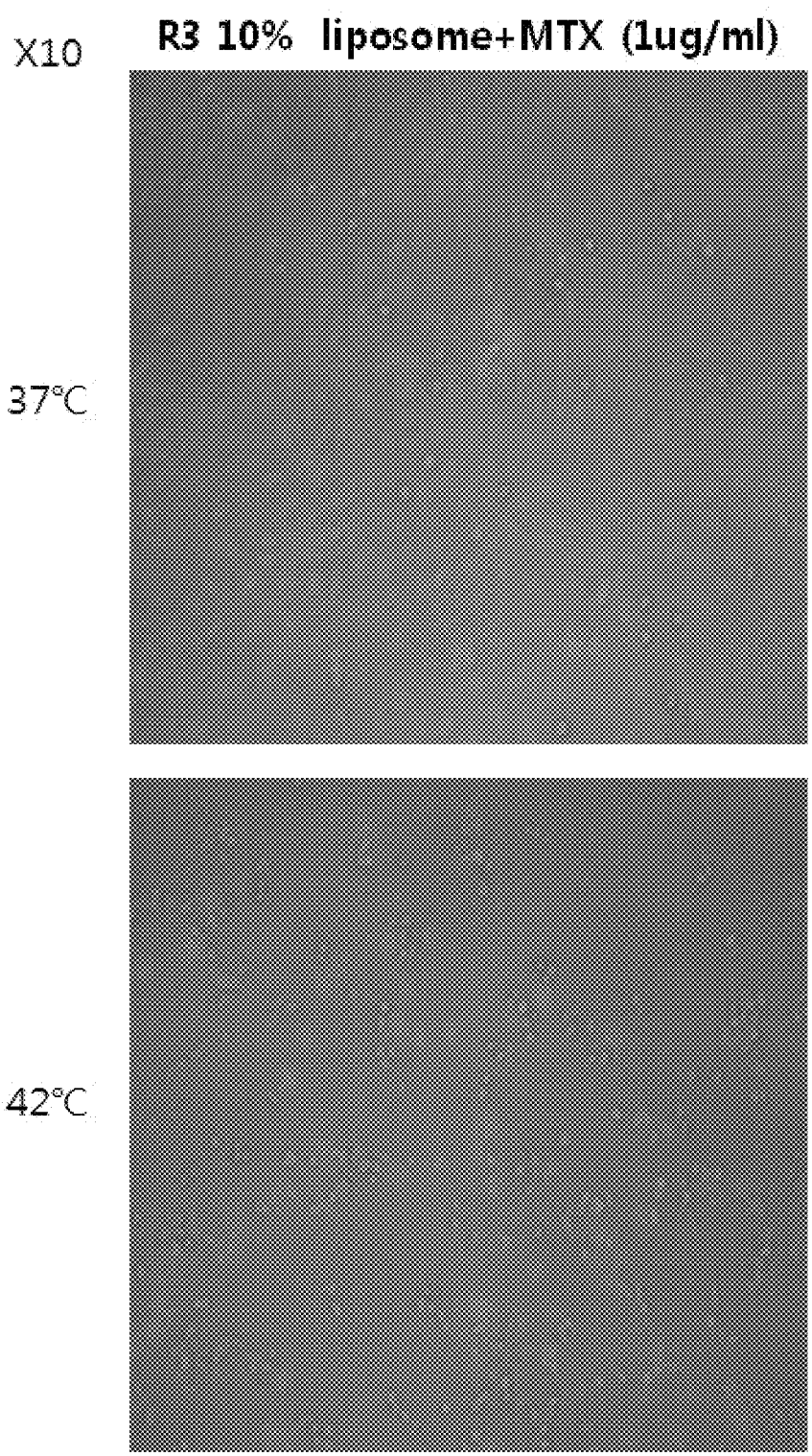

FIGS. 11A and 11B show images of the cells. As shown in FIGS. 11A and 11B, the cells were viable at 37° C. whereas the cell counts were significantly reduced at 42° C. as the liposomes exerted cytotoxicity.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A liposome comprising:
   a lipid bilayer,
   a thermosensitive peptide conjugated to a moiety comprising a hydrophobic group, and
   a cationic lipid,
   wherein the moiety comprising a hydrophobic group is positioned within the lipid bilayer, and
   the moiety comprising a hydrophobic group is a sterol; a sphingolipid; a saturated or unsaturated C4-C30 hydrocarbon; a saturated or unsaturated C4-C30 acyl group; or a saturated or unsaturated C4-C30 alkoxy group, and the moiety comprising a hydrophobic group is conjugated to the thermosensitive peptide by interaction with a functional group of the thermosensitive peptide, wherein the functional group is selected from an amino group, a carbonyl group, a hydroxyl group, a thiol group, and a combination thereof.

2. The liposome of claim 1, wherein the cationic lipid is selected from the group consisting of 1,2-dipalmitoyl-3-trimethyl ammonium-propane (DPTAP), 1,2-dioleyl-3-trimethyl ammonium-propane (DOTAP), N,N-dioleyl-N,N-dimethyl ammoniumchloride (DODAC), N,N-distearyl-N,N-dimethyl ammoniumbromide (DDAB), N-(1-(2,3-dioleoyloxy)propyl-N,N,N-trimethyl ammoniumchloride, N,N-dimethyl-(2,3-dioleoyloxy)propylamine (DODMA), N,N,N-trimethyl-(2,3-dioleoyloxy)propylamine (DOTMA), 1,2-diacyl-3-trimethyl ammonium-propane (TAP), 1,2-diacyl-3-dimethyl ammonium-propane (DAP), 3beta-[N—(N',N',N'-trimethylaminoethane)carbamoyl]cholesterol (TC-cholesterol), 3beta[N—(N',N'-dimethylaminoethane)carbamoyl]cholesterol (DC-cholesterol), 3beta[N—(N'-monomethylaminoethane)carbamoyl]cholesterol (MC-cholesterol), 3beta[N-(aminoethane)carbamoyl]cholesterol (AC-cholesterol), cholesteyloxypropane-1-amine (COPA), N—(N'-aminoethane)carbamoylpropanoic tocopherol (AC-tocopherol), N—(N'-methylaminoethane)carbamoylpropanoic tocopherol (MC-tocopherol), and a combination thereof, or a lipid conjugate in which a fatty acid of C12 to C22 is conjugated with a peptide comprising 1 to 10 repeats of a cationic amino acid selected from the group consisting of arginine, histidine, lysine, and a combination thereof.

3. The liposome of claim 1, further comprising a lipid bilayer stabilizing agent selected from the group consisting of a steroid, a glycolipid, a sphingolipid, or a combination thereof.

4. The liposome of claim 3, wherein the lipid bilayer stabilizing agent is selected from the group consisting of cholesterol, sitosterol, ergosterol, stigmasterol, 4,22-stigmastadien-3-one, stigmasterol acetate, lanosterol, cycloartenol, and a combination thereof.

5. The liposome of claim 1, wherein the thermosensitive peptide is selected from the group consisting of an elastin-like polypeptide (ELP), a leucine zipper, and a combination thereof.

6. The liposome of claim 5, wherein the elastin-like polypeptide comprises 1 to 200 repeats of a repeating unit selected from the group consisting of VPGXG, PGXGV, GXGVP, XGVPG, GVPGX and a combination thereof, wherein V is valine, P is proline, G is glycine, and X in each repeating unit is independently selected from the group consisting of alanine, isoleucine, leucine, methionine, phenylalanine, tryptophan, valine, asparagine, cysteine, glutamine, glycine, serine, threonine, tyrosine, aspartic acid, glutamic acid, arginine, histidine, and lysine.

7. The liposome of claim 5, wherein the leucine zipper is [XSZLESK]$_n$, in which the repeating unit [XSZLESK] is repeated n times, wherein, in each repeating unit, X is independently valine or lysine, Z is independently serine or lysine, and n is an integer of 1 to 200.

8. The liposome of claim 1, wherein a molar ratio of a phospholipid contained in the lipid bilayer and the thermosensitive peptide conjugated to the moiety comprising the hydrophobic group is 99.9:0.1 to 90:10.

9. The liposome of claim 1, wherein the lipid bilayer contains a C12-C22 phospholipid.

10. The liposome of claim 9, wherein the phospholipid is selected from the group consisting of phosphatidyl choline, phosphatidyl glycerol, phosphatidyl inositole, phosphatidyl ethanolamine, and a combination thereof.

11. The liposome of claim 1, wherein the lipid bilayer further comprises a phospholipid derivatized with a hydrophilic polymer.

12. The liposome of claim 11, wherein the hydrophilic polymer is selected from the group consisting of polyethylene glycol, polylactic acid, a copolymer of polylactic acid and polyglycolic acid, polyvinyl alcohol, polyvinyl pyrrolidone, an oligosaccharide, and a combination thereof.

13. The liposome of claim 1, having a phase transition temperature of 38° C. to 45° C.

14. The liposome of claim 1, having an average diameter of 50 nm to 500 nm.

15. The liposome of claim 1, further comprising an anionic drug in an inner space of the liposome, on a surface of the lipid bilayer, or both in an inner space of the liposome and on a surface of the lipid bilayer.

16. A pharmaceutical composition for delivering an anionic drug, comprising:
the liposome of claim 1, and
an anionic drug,
wherein the anionic drug is entrapped in an inner space of the liposome, on a surface of the lipid bilayer, or both in an inner space of the liposome and on a surface of the lipid bilayer.

17. The pharmaceutical composition of claim 16, wherein the anionic drug has a functional group selected from the group consisting of a carboxylate group, a sulfate group, a citrate group, a phosphate group, and a phosphorylated functional group, or a nucleic acid.

18. A method for delivering an anionic drug to a patient, the method comprising administering the pharmaceutical composition of claim 16 to a patient in need thereof.

19. The method of claim 18, further comprising a step of heating a target lesion of the patient to release the drug from the liposome at the target lesion.

20. The method of claim 19, wherein the lesion is heated to a temperature of 38° C. to 45° C.

* * * * *